US008383346B2

(12) United States Patent
Colbeck et al.

(10) Patent No.: US 8,383,346 B2
(45) Date of Patent: *Feb. 26, 2013

(54) COMBINED AUTOMATED PARALLEL SYNTHESIS OF POLYNUCLEOTIDE VARIANTS

(75) Inventors: Jeffrey Colbeck, Menlo Park, CA (US); Benjamin Mijts, Belmont, CA (US); Lorraine Joan Giver, Sunnyvale, CA (US); Richard J. Fox, Kirkwood, MO (US); Vesna Mitchell, San Jose, CA (US); Bumshik Robert Pak, Fremont, CA (US); Lynne Gilson, Encinitas, CA (US)

(73) Assignee: Codexis, Inc., Redwood City, CA (US)

( * ) Notice: Subject to any disclaimer, the term of this patent is extended or adjusted under 35 U.S.C. 154(b) by 407 days.

This patent is subject to a terminal disclaimer.

(21) Appl. No.: 12/562,988

(22) Filed: Sep. 18, 2009

(65) Prior Publication Data

US 2010/0093560 A1   Apr. 15, 2010

Related U.S. Application Data

(63) Continuation-in-part of application No. 12/483,089, filed on Jun. 11, 2009.

(60) Provisional application No. 61/061,581, filed on Jun. 13, 2008.

(51) Int. Cl.
*C12Q 1/68* (2006.01)
*C12P 19/34* (2006.01)
*C07H 21/04* (2006.01)

(52) U.S. Cl. .................... 435/6.12; 536/24.33; 435/91.2

(58) Field of Classification Search ........................ None
See application file for complete search history.

(56) References Cited

U.S. PATENT DOCUMENTS

| | | |
|---|---|---|
| 5,023,171 A | 6/1991 | Ho |
| 5,830,696 A | 11/1998 | Short |
| 5,939,250 A | 8/1999 | Short |
| 5,965,408 A | 10/1999 | Short |
| 6,153,410 A | 11/2000 | Arnold et al. |
| 6,171,820 B1 | 1/2001 | Short |
| 6,335,179 B1 | 1/2002 | Short |
| 6,358,709 B1 | 3/2002 | Short et al. |
| 6,361,988 B1 * | 3/2002 | Arnold et al. ................ 435/196 |
| 6,479,258 B1 | 11/2002 | Short |
| 6,489,145 B1 | 12/2002 | Short |
| 6,562,594 B1 | 5/2003 | Short |
| 6,582,914 B1 | 6/2003 | Caldwell et al. |
| 6,605,449 B1 | 8/2003 | Short |
| 6,713,279 B1 | 3/2004 | Short |
| 6,764,835 B2 | 7/2004 | Short |
| 6,884,583 B2 | 4/2005 | Livak et al. |
| 7,402,383 B2 | 7/2008 | Bovenberg |

| | | |
|---|---|---|
| 2003/0054383 A1 | 3/2003 | Bass et al. |
| 2006/0160138 A1 | 7/2006 | Church et al. |
| 2009/0312196 A1 * | 12/2009 | Colbeck et al. ................ 506/16 |

FOREIGN PATENT DOCUMENTS

| | | |
|---|---|---|
| EP | 1409667 | 12/2004 |
| EP | 1341909 B1 | 5/2005 |
| JP | 2005-095083 A | 4/2005 |
| WO | WO95/22625 | 8/1995 |
| WO | WO97/20078 | 6/1997 |
| WO | WO98/27230 | 6/1998 |
| WO | WO98/42832 | 10/1998 |
| WO | WO00/18906 | 4/2000 |
| WO | WO00/42560 | 7/2000 |
| WO | WO00/42561 | 7/2000 |
| WO | WO01/75767 | 10/2001 |
| WO | 03/010183 A2 | 2/2003 |
| WO | WO2006/105082 A2 * | 10/2006 |

OTHER PUBLICATIONS

An, Y. et al. A rapid and efficient method for multiple-site mutagensesis with a modified overlap extension PCR. Appl. Microbiol. Biotechnol., vol. 68, p. 774-778, 2005.*
Ho, S.N. et al. Site-directed mutagenesis by overlap extension using the polymerase chain reaction. Gene, vol. 77 (1), p. 51-59, 1989.*
Cox, J. C., et al., 2007 "Protein fabrication automation", *Protein Sci*.16:1-12.
Gao, X. et al., 2003 "Thermodynamically balanced inside-out (TBIO) PCR-based gene synthesis: a novel method of primer design for high-fidelity assembly of longer gene sequences", *Nucleic Acids Research*, vol. 31:22, 1-11.
Ge, L. et al., 1997 "Simultaneous introduction of multiple mutations using overlap extension PCR", *BioTechniques* 22:28-30.
Stemmer, W., et al., 1995 "Single-step assembly of a gene and entire plasmid from large numbers of oligodeoxyribonucleotides", *Gene*, 164:49-53.
Brissos, V. et al., 2008 "Improving activity and stability of cutinase towards the anionic detergent AOT by complete saturation mutagenesis", *Protein Engineering, Design & Selection* 1-7.
Uchiyama, H., et al., 1999 "Mutation Scrambling for in vitro evolution to improve thermostability of prolyl endopeptidase", Bio R & D 16:27-35.
Uchiyama, H., et al., 1999 "Mutation Scrambling for in vitro evolution to improve thermostability of prolyl endopeptidase", Bio R & D 16:27-35 (English Translation of Japanese language reference).
Hamamatsu, N., et al., 2005 "Biased mutation-assembling: an efficient method for rapid directed evolution through simultaneous mutation accumulation", *Protein Engineering, Design & Selection* 18:265-271.
Aita, T., et al., 2005 "Surveying a local fitness landscape of a protein with epistatic sites for the study of directed evolution", *Biopolymers*, 64: 95-105.

(Continued)

*Primary Examiner* — Prabha Chunduru
(74) *Attorney, Agent, or Firm* — Codexis, Inc.

(57) ABSTRACT

The present disclosure relates to methods for efficient synthesis, cloning, transformation and screening of large diverse libraries of polynucleotide variants comprising well-defined nucleotide differences relative to a reference polynucleotide.

25 Claims, 6 Drawing Sheets

OTHER PUBLICATIONS

Higuchi, R., et al., 1988 "A general method of in vitro preparation and specific mutagenesis of DNA fragments: study of protein and DNA interactions", *Nucleic Acids Research* vol. 16:15 7351-7367.

Faham, M., et al. PNAS vol. 102(41):14717-14722(2005) "Multiplexed variation scanning for 1000 amplicons in hundreds of patients using mismatch repair detection (MRD) on tag arrays".

Notification of Transmittal of the International Search Report and the Written Opinion of the International Searching Authority, or the Declaration, PCT/US2009/047046, mailed Nov. 10, 2009.

Ho, S.N., et al., "Site-directed mutagenesis by overlap extension using the polymerase chain reaction," Gene, 77 (1):51-59 [1989].

Jensen, P.H., et al., "Combination primer polymerase chain reaction for multi-site mutagenesis of close proximity sites", J. Biomolecular Techniques, 16:334-338 [2005].

Urban, A., et al., "A rapid and efficient method for site-directed mutagenesis using one-step overlap extension PCR," Nucleic Acids Research, 25(11):2227-2228 [1997].

Wataru, I., et al., "A general method for introducing a series of mutations into cloned DNA using the polymerase chain reaction," Gene, 102:67-70 [1991].

An, Y., et al., "A rapid and efficient method for multiple-site mutagenesis with a modified overlap extension PCR," Appl. Microbiol. Biotechnol., 68:774-778 [2005].

Fox, R.J., et al., "Improving catalytic function by ProSAR-driven enzyme evolution," Nature Biotechnology, 25 (3):338-344 [2007].

Sawano, A., et al., "Directed evolution of green fluorescent protein by a new versatile PCR strategy for site-directed and semi-random mutagenesis," Nuc Acid Res, 28(16):e78 [2000].

\* cited by examiner

US 8,383,346 B2

COMBINED AUTOMATED PARALLEL SYNTHESIS OF POLYNUCLEOTIDE VARIANTS

1. CROSS REFERENCE TO RELATED APPLICATIONS

This application is a continuation-in-part of U.S. patent application Ser. No. 12/483,089, filed Jun. 11, 2009, which claims priority from U.S. provisional application 61/061,581, filed Jun. 13, 2008, each of which is hereby incorporated by reference herein.

2. BACKGROUND

Various techniques of in silico and in vitro based directed evolution of protein function have allowed the generation of proteins with novel properties. For example, cytochrome P450 enzymes have been evolved to have activity against substrates not normally recognized by the naturally occurring enzyme (see, e.g., Landwehr et al., 2007, Chem Biol 14(3): 269-78; Kubo et al., 2006, Chemistry 12(4):1216-20.). Typically, for generating such new enzymes, a polynucleotide encoding a reference polypeptide, such as a wild type enzyme, is subjected to mutagenesis to generate polynucleotides encoding polypeptide variants with changes in amino acid sequence. Screening of the variants for a desired property, such as an improvement in an enzyme stability or activity against new substrates, allows the identification of the amino acid residues associated with the changed property. However, not all combinations of the mutations will be present in the population of screened variants. For example, a mutation associated with thermal stability of an enzyme may not be found in association with a mutation associated with a change in substrate specificity. This bias in the population can arise from various factors, including, among others, the parental amino acid sequence encoded by the polynucleotide used for mutagenesis, possible selection against the combination during in vivo propagation of the polynucleotide, and the bias in the technique used for mutagenesis (e.g., use of polymerases to introduce errors).

Because the mutations at defined amino acid residue positions of a reference polypeptide sequence can provide a wealth of information about the polypeptide's biological activities, once mutations have been initially identified, it is desirable to prepare various combinations of the mutations not found in the initial set of screened variants that can be tested for the desired property. In silico based selection of defined mutations or sets of mutations provide a framework for generating a large number of possible mutation combinations. For example, mutations affecting substrate specificity can be combined with mutations affecting other enzyme properties, including, among others, enzyme activity, thermal stability, and inhibitor resistance. Typically, the approach to generating these polypeptides having novel combinations of mutations is to synthesize individual species (i.e., synthesis of each polynucleotide encoding the mutant gene). This can be accomplished by chemical and/or enzymatic synthesis of the polynucleotide in combination with standard recombination techniques. Such de novo synthesis techniques require whole gene synthesis of each polynucleotide variant and/or synthesis of large numbers of oligonucleotide primers which are then used to synthesize whole polynucleotide variant (e.g., via ION-PCR). These techniques require more oligonucleotide syntheses and result in lower yields of variants having the correct sequence. Consequently, if the data set of mutations is large, the cost and efficiency of generating the mutation combinations can limit the ability to screen a large number of novel combinations. Thus, efficient and cost effective methods of generating polynucleotides encoding combinations of defined mutations are desirable.

3. SUMMARY

The present disclosure relates to methods of efficiently generating polynucleotides having different combinations of defined sequence changes (e.g., desired amino acid mutations) as compared to a reference polynucleotide sequence. The methods are based on use of a library of polynucleotide fragments (i.e., amplicons) that have overlapping adjacent regions such that sets of the polynucleotide fragments can be assembled to generate a plurality of polynucleotide variants each having a defined set of sequence changes. Selected forward and reverse primers are used to introduce the sequence changes by amplifying a reference polynucleotide template and thereby generate polynucleotide fragments comprising the defined sequence changes. The library is designed to have sufficient polynucleotide fragments to assemble at least two different polynucleotide variant sequences. In some embodiments, the library of polynucleotide fragments contain members that have all of the defined differences in a polynucleotide sequence (e.g., desired nucleotide changes) as compared to a reference sequence such that all sequence permutations can be assembled. In some embodiments, the polynucleotides can be designed to encode polypeptides having defined differences in amino acid sequence as compared to a reference amino acid sequence.

The methods of the present disclosure are capable of producing large libraries of polynucleotide variant sequences having defined nucleotide differences (e.g., libraries of 10, 50, 100, 150, 300, 500, 700, 1000 or more variants, each having 1, 2, 3, 5, 9, 12, 15, 20, 25, 30, 35, 40, 50, or more, desired changes), with relatively few (e.g., compared to whole gene synthesis methods), and relatively short (e.g., 35-mer or less) oligonucleotides, and wherein the average percentage of correct sequences is surprisingly high (e.g., at least 65%, 75%, 85%, 95%, or more).

In some embodiments, the method of forming polynucleotides encoding polypeptide variants can comprise: selecting a plurality of defined amino acid residue differences relative to a reference amino acid sequence; defining overlapping segments of a polynucleotide sequence encoding the polypeptide with the different amino acid sequence or the reference amino acid sequence, each segment being bounded by a set of forward and reverse primer binding sequences and wherein a polynucleotide sequence difference encoding each of the plurality of amino acid residue differences is encompassed in the primer binding sequence; amplifying each segment with the set of forward and reverse primers, wherein selected forward and/or reverse primers contain the polynucleotide sequence differences, to generate a library of amplicons comprising members encoding the amino acid residue differences, wherein the library comprises members for assembling two or more different amino acid sequence permutations of the defined amino acid differences; assembling from the library a set of amplicons having complementary overlapping adjacent regions, wherein the set of amplicons together encode the polypeptide with a defined amino acid sequence permutation having one or more amino acid residue differences; and replicating the set of assembled amplicons to synthesize the polynucleotide encoding the polypeptide.

Further described herein are methods of generating the polynucleotide fragment library, where the method comprises: (a) generating a plurality of permutations of amino acid sequences differing from a reference amino acid sequence based on a plurality of defined amino acid residue differences from the reference amino acid sequence, and for each permutation; (i) determining a polynucleotide sequence encoding the amino acid sequence permutation based on a reference polynucleotide sequence; (ii) identifying a change in polynucleotide sequence encoding an amino acid residue difference as compared to a reference amino acid sequence, and determining the proximity of a nearest-neighbor change in polynucleotide sequence encoding another amino acid residue difference in the amino acid sequence permutation; (iii) selecting a forward oligonucleotide primer having a sequence encoding the amino acid residue difference, and optionally including the nearest-neighbor change in polynucleotide sequence in the same forward oligonucleotide primer if proximate to the first change in polynucleotide sequence; (iv) identifying the next change in polynucleotide sequence or until the end of the polynucleotide is reached, and selecting a reverse oligonucleotide primer for amplifying a polynucleotide fragment with the forward oligonucleotide primers, wherein the reverse primer optionally encodes the next change in amino acid residue difference; (v) reiterating steps (ii) to (iv) for each change in polynucleotide sequence encoding an amino acid residue difference such that all changes in the polynucleotide sequence are present on oligonucleotide primers; and (b) amplifying with each set of forward and reverse oligonucleotide primers to generate the library of overlapping amplicons having members encoding amino acid residue differences.

In another aspect, the present disclosure provides a library of such polynucleotide fragments (i.e., amplicons) that can be used for assembling the polynucleotide variants. In some embodiments, the plurality of polynucleotide fragments comprises polynucleotide fragments with overlapping adjacent regions, each polynucleotide fragment being bounded by primer binding sequences for forward and reverse primers, wherein the plurality of polynucleotide fragments have members that encode in the primer binding sequences a specific amino acid residue difference from a defined plurality of amino acid residue differences relative to a reference amino acid sequence such that the plurality of polynucleotide fragments encode all of a selected plurality of amino acid residue differences from the defined plurality of amino acid residue differences; and wherein the plurality of polynucleotide fragments comprise members for assembling two or more different amino acid sequence permutations of the defined amino acid differences. In some embodiments, the plurality of polynucleotide fragments comprises members sufficient for assembling all of the possible amino acid sequence permutations of the selected plurality of amino acid residue differences.

In another aspect, the present disclosure provides a method of synthesizing a plurality of polynucleotide variants each having a defined nucleotide difference relative to a reference polynucleotide sequence, wherein the method comprises: (a) separately amplifying a reference polynucleotide template with each of a plurality of pairs of forward and reverse primers, wherein the plurality of pairs of forward and reverse primers comprises the plurality of defined nucleotide differences and wherein each pair generates an amplicon comprising a sequence capable of binding to an adjacent overlapping sequence of at least one other amplicon; (b) separately assembling a plurality of sets of amplicons, wherein each set comprises amplicons having adjacent overlapping sequences capable of binding to form the full length of the reference polynucleotide sequence; and (c) replicating the plurality of sets of assembled amplicons, thereby synthesizing a plurality of polynucleotide variants.

In another embodiment, the disclosure provides a method of synthesizing a plurality of polynucleotide variants each having a defined nucleotide difference relative to a reference polynucleotide sequence, the method comprising: (a) selecting a plurality of defined nucleotide differences relative to the reference polynucleotide sequence; (b) defining a plurality of segments of the reference polynucleotide sequence, wherein each segment overlaps at least one adjacent segment and is bounded by a pair of forward and reverse primer binding sequences, wherein the forward and/or reverse primers comprise at least one of the plurality of defined nucleotide differences; (c) separately amplifying a reference polynucleotide template with each of a plurality of pairs of forward and reverse primers, wherein each pair of primers comprises at least one of the plurality of defined nucleotide differences, thereby generating an addressable library of amplicons each corresponding to a segment of the reference polynucleotide sequence having a defined nucleotide differences; (d) separately assembling a plurality of sets of amplicons from the addressable library of amplicons, wherein each set comprises amplicons corresponding to overlapping adjacent segments that comprise the full length of the reference polynucleotide sequence; and (e) replicating the plurality of sets of assembled amplicons, thereby synthesizing a plurality of polynucleotide variants.

In some embodiments of the methods of synthesizing a plurality of polynucleotide variants, after they are separately assembled and replicated (e.g., via SOE-PCR), the polynucleotide variants are combined (i.e., pooled) rather than maintained separately (e.g., in an addressable array). The pool is then cloned into an expression vector, transformed into cells, and plated, which provides a surprising advantage by facilitating screening of large libraries comprising hundreds or thousands of full-length variants having defined nucleotide differences, followed by sequencing limited to only those variants encoding polypeptides having some desired level of activity or other improved property. Thus, in some embodiments the method of synthesizing a plurality of polynucleotide variants each having at least one defined nucleotide difference relative to a reference polynucleotide sequence, comprises: (a) separately amplifying a reference polynucleotide template with each of a plurality of pairs of forward and reverse primers, wherein the plurality of pairs of forward and reverse primers comprises the plurality of defined nucleotide differences and wherein each pair generates an amplicon comprising a sequence capable of binding to an adjacent overlapping sequence of at least one other amplicon; (b) separately assembling a plurality of sets of amplicons, wherein each set comprises amplicons having adjacent overlapping sequences capable of binding to form the full length of the reference polynucleotide sequence; (c) replicating the plurality of sets of assembled amplicons; and (d) combining the plurality of polynucleotide variants, thereby synthesizing a pool comprising a combined plurality of polynucleotide variants, each having a defined nucleotide difference. In some embodiments of the method the reference polynucleotide encodes a reference polypeptide and each of the plurality of polynucleotide variants encodes a polypeptide having at least one amino acid sequence difference. In other embodiments, the method further comprises after the step of combining the plurality of polynucleotide variants: (e) a step of cloning the combined plurality of polynucleotide variants into an expression vector, thereby generating a combined plurality of expression vectors each comprising a polynucleotide variant; (f) transforming cells with the combined plurality of expression vectors; (g) screening the transformed cells for activity of the polypeptides encoded by the polynucleotide variants; (h) sequencing polynucleotide variants that encode polypeptides having activity; or (i) isolating at least one polypeptide encoded by the polynucleotide variants.

In some embodiments, the disclosure provides methods of screening an addressable library of polynucleotide variants encoding polypeptides, the method comprising: (a) combining members of the addressable library of polynucleotide variants into a pool; (b) cloning the pool of polynucleotide variants into an expression vector; (c) transforming cells with the expression vector; (d) plating the transformed cells to generate a plurality of separate clones comprising the library of polynucleotide variants; and (e) screening the clones for an improved property relative to a reference polypeptide. In some embodiments of the method of screening, the method is carried out wherein the addressable library of polynucleotide variants comprises at least 50, 100, 200, 300, 400, 500, 600, 700, 800, 900, 1000, or more different polynucleotide variants. In some embodiments of the method of screening, the method is carried out wherein the addressable library of polynucleotide variants comprises at least 100, 200, 400, 800, 1000, or more different polynucleotide variants each comprising a different defined nucleotide difference at one of at least 5, 10, 20, 40, 50, or more different selected positions, respectively. In some embodiments of the method of screening, the method is carried out wherein the addressable library of polynucleotide variants comprises at least 460 different polynucleotide variants each comprising one of 23 different codons at one of 20 different selected positions. In some embodiments of the above methods of screening, at least 75%, at least 80%, at least 85%, at least 90%, at least 95%, or more of the addressable library of polynucleotide variants comprise the correct sequence.

In other embodiments, the present disclosure provides a method of synthesizing a plurality of polynucleotide variants having a stochastic mix of defined nucleotide differences relative to a reference polynucleotide sequence. Such an embodiment provides the facile ability to create combinatorial libraries of polynucleotide variants having stochastic combinations of defined nucleotide differences. The method comprises: (a) providing a plurality of pairs of forward and reverse primers, wherein the plurality of pairs of forward and reverse primers comprises a mixture of mutagenic and non-mutagenic primers, wherein the mutagenic primers comprise a plurality of defined nucleotide differences, and wherein each pair generates an amplicon comprising a sequence capable of binding to an adjacent overlapping sequence of at least one other amplicon; (b) amplifying a reference polynucleotide template with each of the plurality of pairs of forward and reverse primers, thereby generating a plurality of sets of amplicons, wherein each set comprises amplicons having adjacent overlapping sequences capable of binding to form the full length of the reference polynucleotide sequence; and (c) assembling and replicating the plurality of sets of the amplicons, thereby synthesizing a plurality of polynucleotide variants having a stochastic mix of defined nucleotide differences. In another embodiment, this method can be carried out wherein the plurality of pairs of forward and reverse primers is combined prior to amplifying the reference polynucleotide template, thereby generating a combined plurality of sets of amplicons. In another embodiment, this method can be carried out wherein amplifying the reference polynucleotide template is carried out separately with each of the plurality of pairs of forward and reverse primers, and the plurality of sets of amplicons is combined prior to assembling and replicating.

In some embodiments of the methods of synthesizing a plurality of polynucleotide variants disclosed herein, the methods can be carried out wherein the reference polynucleotide encodes a reference polypeptide and each of the plurality of polynucleotide variants encodes a polypeptide having at least one amino acid sequence difference. In additional embodiments, the methods can be carried out wherein it further comprises the steps of: (i) cloning each of the plurality of polynucleotide variants into an expression vector; (ii) transforming cells with the expression vectors; (iii) screening the transformed cells for activity of the polypeptides encoded by the polynucleotide variants; or (iv) isolating at least one polypeptide encoded by the polynucleotide variants. Additionally, the methods can be carried out wherein each polynucleotide variant is assembled at a known position on an array.

In other embodiments of the methods of synthesizing a plurality of polynucleotide variants, the methods can be carried out wherein a plurality of different amino acid changes are encoded at one or more of the targeted positions in a polypeptide. In such an embodiment, the plurality of pairs of forward and reverse primers comprise degenerate primers (e.g., a set of primers having a degenerate codon at the same position in each of the primer sequences) encoding a plurality amino acid differences at a single position in the polypeptide. For example, in some embodiments the degenerate primers can comprise a set of primers having degenerate codons selected from the group consisting of NHT, NNB, NNG, NNK, NNN, NNS, NNT, NDT, RMG, RNG, RRS, SNT, VNS, VNT, and VWG. In some embodiments, the methods can be carried out wherein the plurality of different codons consists of the degenerate codons NNT and VWG, and the codon TGG. These codons encode all 20 natural amino acids with only 23 codons. In some embodiments, different degenerate codons can be used for amino acid differences at different positions of the polynucleotide. For example, at one position degenerate primers encoding all 20 amino acids may be used, while at another position degenerate primers encoding only 16 or fewer amino acids can be used.

In some embodiments of the methods of synthesizing a plurality of polynucleotide variants disclosed herein, the methods can be carried out wherein sequences of the plurality of forward and reverse primer sequences are generated by the steps of: (i) identifying a first defined difference in the polynucleotide variant sequence as compared to the reference sequence, and determining the proximity of a nearest-neighbor defined difference in the polynucleotide sequence; (ii) selecting a forward primer having a sequence comprising the first defined nucleotide difference, and optionally including any nearest-neighbor defined difference in the same forward primer if proximate to the first defined nucleotide difference; (iii) identifying a next defined difference in the polynucleotide variant sequence as compared to the reference sequence, and determining the proximity of a nearest-neighbor defined difference in the polynucleotide sequence, or identifying that the end of the polynucleotide variant has been reach; (iv) selecting a reverse primer having a sequence comprising the next defined nucleotide difference, and optionally including any nearest-neighbor defined difference in the same forward primer if proximate to the next defined nucleotide difference; and (v) repeating steps (iii) to (iv) for each defined difference in the polynucleotide variant sequence such that all defined difference are present on primers.

In some embodiments of the methods of synthesizing a plurality of polynucleotide variants disclosed herein, the plurality of polynucleotide variants comprises at least 10, 25, 35, 50, 75, 90, 120, 150, 180, 300, 500, 700, 900, or even more different polynucleotide variants.

In some embodiments of the methods of synthesizing a plurality of polynucleotide variants disclosed herein, at least one of the plurality of polynucleotide variants comprises at least 2, 3, 6, 9, 12, 15, 18, 21, 24, 27, 30, or even more defined nucleotide differences relative to the reference polynucleotide sequence. In some embodiments, two or more, or in some embodiments each of the plurality of polynucleotide variants comprises at least 1, 2, 3, 6, 9, 12, 15, 18, 21, 24, 27, 30, or even more defined nucleotide differences relative to the reference polynucleotide sequence.

In some embodiments of the methods, the plurality of polynucleotide variants synthesized using the methods can comprise at least 10, 20, 30, 40, 50, 100, 200, or more different polynucleotide variants, wherein each variant comprises a different defined nucleotide difference at one of 10, 20, 30, 40, 50, 100, 200, or more different selected positions (i.e., 10, 20, 30, 40, 50, 100, 200, or more distinct single site mutants). Much larger scale diversity is also accessible, for example when using degenerate primers the method can provide "saturation mutagenesis" libraries wherein each polynucleotide variant member has a different sequence comprising one of 23 different codons at a different selected position of the reference polynucleotide sequence. Accordingly, the methods disclosed herein can be used to synthesize plurality of polynucleotide variants comprising at least 23, 46, 69, 92, 115, 230, 460, 920 or more different polynucleotide variants each comprising one of 23 different codons at one of 1, 2, 3, 4, 5, 10, 20, 40, or more different selected positions. In some embodiments, the methods can be carried out wherein different sets of specific and/or degenerate codons are used at different selected positions for defined nucleotide differences in the plurality of forward and reverse primers, thereby providing diverse libraries of polynucleotide variants having well-defined mutations.

In some embodiments of the methods of synthesizing a plurality of polynucleotide variants disclosed herein, at least one of the plurality of sets of amplicons comprises at least 3, at least 5, at least 7, at least 10, or more different amplicons. In some embodiments, two or more, or in some embodiments each of the plurality of sets of amplicons comprises at least 3, at least 5, at least 7, at least 10, or more different amplicons. In embodiments where degenerate primers are used, the resulting amplicons are degenerate. Accordingly, in some embodiments at least one of the plurality of sets of amplicons comprises at least 3, at least 5, at least 7, at least 10, or more different degenerate amplicons.

In some embodiments of the methods of synthesizing a plurality of polynucleotide variants disclosed herein, the length of the reference polynucleotide sequence is at least 500 bp, 750 bp, 1000 bp, 1250 bp, 1500 bp, or even longer.

In some embodiments of the methods of synthesizing a plurality of polynucleotide variants disclosed herein, the plurality of pairs of forward and reverse primers comprises 400 or fewer, 300 or fewer, 200 or fewer, 100 or fewer, 50 or fewer, or even 25 or fewer. In some embodiments, the plurality of pairs of forward and reverse primers comprises from 6 to about 200, from 6 to about 150, from 6 to about 100, from 6 to about 50, 6 to about 40, 6 to about 30, 6 to about 25, 6 to about 20, 6 to about 15, or even fewer different oligonucleotides, and wherein the lengths of the oligonucleotides are from about 20 to about 50 nucleotides, about 20 to about 40 nucleotides, or about 25 to about 35 nucleotides.

In some embodiments of the methods of synthesizing a plurality of polynucleotide variants disclosed herein, the average percentage of the synthesized plurality of polynucleotide variants comprising the correct sequence is at least about 65%, 70%, 75%, 80%, 85%, 90%, or 95%, or more. Accordingly, in any of the embodiments of the method disclosed herein are capable of synthesizing libraries of polynucleotide variants having high levels diversity (distinct nucleotide differences at different selected positions) with very well-defined accuracy of at least about 65%, 75%, 85%, or 95%, or more correct sequences.

In some embodiments, the disclosure provides methods of synthesizing a plurality of polynucleotide variants wherein any of the above described parameters (e.g., number of variants, number of defined nucleotide differences, length of the reference polynucleotide sequence, number of pairs of forward and reverse primers, length of primer oligonucleotides, and/or percentage of full length perfect sequences) are combined.

In addition to the above methods, the disclosure also provides an addressable library of polynucleotide variants comprising a plurality of polynucleotide variants or amplicons synthesized according to any of the above methods. Accordingly, in some embodiments the disclosure provides an addressable library of amplicons, wherein each member of the library of amplicons comprises at least one defined nucleotide difference relative to a reference polynucleotide sequence and an overlapping adjacent region capable of binding to the overlapping adjacent region of at least one other amplicon in the library, and wherein the plurality of amplicons comprise at least one set of amplicons capable of binding to form the full length of the reference polynucleotide sequence. In some embodiments, the addressable library of amplicons comprises members for assembling two or more different polynucleotide variants comprising defined nucleotide differences relative to the reference polynucleotide sequence. In some embodiments of the addressable library of amplicons, the reference polynucleotide sequence encodes a reference polypeptide and the plurality of amplicons comprises members sufficient for assembling all of the possible nucleotide differences encoding a selected plurality of amino acid residue differences.

In other embodiments, the disclosure provides compositions comprising a plurality of polynucleotide variants having defined nucleotide differences, wherein the polynucleotide variants are synthesized according to the methods disclosed herein. Accordingly in some embodiments, the disclosure provides a composition comprising a plurality of expression vectors comprising polynucleotide variants synthesized or a plurality of transformed cells comprising polynucleotide variants synthesized according to the methods disclosed above.

In another embodiment the disclosure provided a library of polypeptide variants isolated according the methods of synthesizing polynucleotide variants encoding polypeptides, followed by cloning the variants into expression vectors, transforming cells, and expressing polypeptide in the transformants.

Further provided herein are computer implemented methods for carrying out various steps of the methods described herein.

4. BRIEF DESCRIPTION OF THE FIGURES

FIG. 1 shows a standard technique for generating polynucleotides encoding defined polypeptide variants (at left) as compared to the method described herein for using libraries of overlapping polynucleotide fragments (at right).

FIG. 2 provides a sample workflow scheme for generating libraries of overlapping polynucleotide fragments based on generating oligonucleotide primers for overlapping segments of a polynucleotide and use of the oligonucleotides in PCR reactions to generate libraries of overlapping polynucleotide fragments.

5. DETAILED DESCRIPTION

Figure 1:
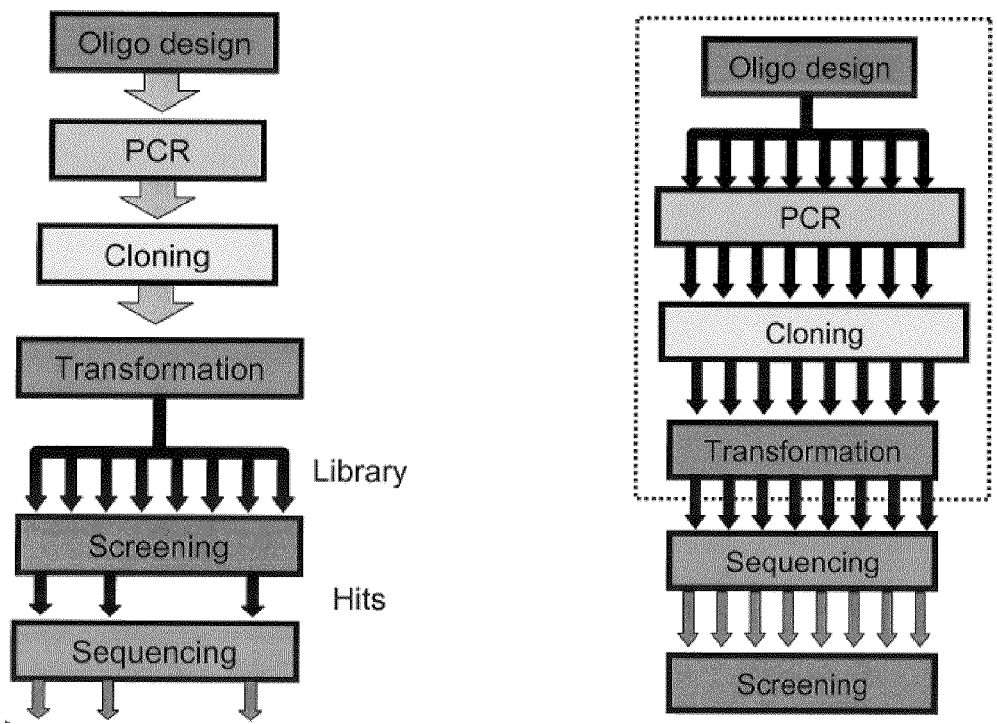

As used in this specification and the appended claims, the singular forms "a", "an" and "the" include plural referents unless the context clearly indicates otherwise. Thus, for example, reference to "a protein" includes more than one protein, and reference to "a compound" refers to more than one compound.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The section headings used herein are for organizational purposes only and not to be construed as limiting the subject matter described. As used herein, the following terms are intended to have the following meanings.

5.1 DEFINITIONS

"Amplifying" and "amplification" as used herein incorporates its common usage and refers to the use of any suitable amplification methodology for generating or detecting any polynucleotide, recombinant or naturally expressed, amenable to amplification in vivo or in vitro, such as by polymerase chain reaction (PCR).

"Amplicon" refers to the product of the amplification reaction generated through the extension of either or both of a pair of amplification primers. An amplicon may contain exponentially amplified nucleic acids if both primers utilized hybridize to a target sequence. Alternatively, amplicons may be generated by linear amplification if one of the primers utilized does not hybridize to the target sequence. Thus, this term is used generically herein and does not imply the presence of exponentially amplified nucleic acids.

"Annealing" or "hybridization" refers to the base-pairing interactions of one nucleobase polymer with another that results in the formation of a double-stranded structure, a triplex structure or a quaternary structure. Annealing or hybridization can occur via Watson-Crick base-pairing interactions, but may be mediated by other hydrogen-bonding interactions, such as Hoogsteen base pairing.

"Assembling" refers to bringing together a plurality of polynucleotide fragments (e.g., amplicons) under conditions in which complementary regions between polynucleotides can anneal to form a hybridization complex, e.g., having a double stranded hybridized region with overhangs for the non-complementary regions. A plurality of polynucleotides can be assembled to form a larger polynucleotide that encodes a polypeptide of interest.

"Bridging polynucleotide" refers to a polynucleotide having complementary regions at the terminal regions such that one polynucleotide can anneal to one terminal region and another polynucleotide can anneal to the other terminal region of the bridging polynucleotide.

"Coding sequence" refers to that portion of a nucleic acid (e.g., a gene) that encodes an amino acid sequence of a protein.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome.

"Complementary" refers to the hybridization or base pairing between nucleotides or nucleic acids, such as, for instance, between the two strands of a double stranded DNA molecule or between an oligonucleotide primer and a primer binding site on a single stranded polynucleotide to be sequenced or amplified. Complementary nucleotides are, generally, A and T (or A and U), or C and G. Two single stranded RNA or DNA molecules are said to be substantially complementary when a polynucleotide (RNA or DNA) strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, e.g., M. Kanehisa, 1984, Nucleic Acids Res. 12:203, incorporated herein by reference. "Complementary to" is used herein to mean that the complementary sequence is substantially identical or identical to the reverse-complement of all or a portion of a reference polynucleotide sequence or that each nucleotide in one strand is able to form a base-pair with a nucleotide, or analog thereof in the opposite strand.

"Conservative amino acid substitutions" refer to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, isoleucine, and methionine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine, arginine, and histidine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Control sequence" refers to a polynucleotide sequence used to effect the expression of coding and non-coding sequences to which they are associated. The nature of such control sequences differs depending upon the host organism. Control sequences generally include promoter, ribosomal binding site, and transcription termination sequence. The term "control sequences" is intended to include components whose presence can influence expression, and can also include additional components whose presence is advantageous, for example, leader sequences and fusion partner sequences.

"Defined difference" as used herein in the context of a mutations to a polynucleotide or polypeptide sequence refers to an a priori specified, selected, and/or desired change to the sequence (e.g., a nucleotide change from c to g in a selected position of a polynucleotide sequence that results in a different amino acid at a desired position of the encoded polypeptide).

"Degenerate codon" as used herein refers to a codon used to represent a set of different codons (also referred to as an "ambiguous codon"). For example, the degenerate codon "NNT" represents a set of 16 codons having the base triplet sequence (A, C, T, or G)/(A, C, T, or G)/T, which encodes a set of the 15 different amino acids: F, S, Y, C, L, P, H, R, I, T, N, V, A, D, and G. Exemplary degenerate codons well-known in the art and useful in methods of the present disclosure include: NHT, NNB, NNG, NNK, NNN, NNS, NNT, NDT, RMG, RNG, RRS, SNT, VNS, VNT, and VWG.

"Deletion" with respect to a polypeptide or polynucleotide refers to the removal of one or more amino acids or nucleotides from the reference polypeptide or polynucleotide, respectively. Deletions can comprise removal of 1 or more amino acids or nucleotides, 2 or more amino acids or nucleotides, 3 or more amino acid or nucleotides, 5 or more amino acids, 6 or more amino acids or nucleotides, 10 or more amino acids or nucleotides, 15 or more amino acids or nucleotides, or 20 or more amino acids or nucleotides, up to 10% of the total number of amino acids or nucleotides, or up to 20% of the total number of amino acids or nucleotides making up the reference polypeptide or polynucleotide. Deletions can be directed to the internal portions and/or terminal portions of the polypeptide or polynucleotide. In various embodiments, the deletion can comprise a continuous segment or can be discontinuous.

"Heterologous" when used with reference to a nucleic acid or polypeptide, indicates that a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature; e.g., a nucleic acid open reading frame (ORF) of the invention operatively linked to a promoter sequence inserted into an expression cassette, e.g., a vector.

"Insertion" or "Addition" refers to a change in a nucleotide or amino acid sequence by the addition of one or more nucleotides or amino acid residues, respectively, as compared to a reference sequence, such as for example, a wild type sequence.

"Library" refers to a set (e.g., a plurality) of heterogeneous polypeptides or nucleic acids. A library is composed of members, each of which has a single polypeptide or nucleic acid sequence. To this extent, "library" is synonymous with "repertoire". Sequence differences between library members are responsible for the diversity present in the library. The library may take the form of a simple mixture of polypeptides or nucleic acids, or may be in the form organisms or cells, for example bacteria, viruses, animal or plant cells and the like, transformed with a library of nucleic acids.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

Figure 2:
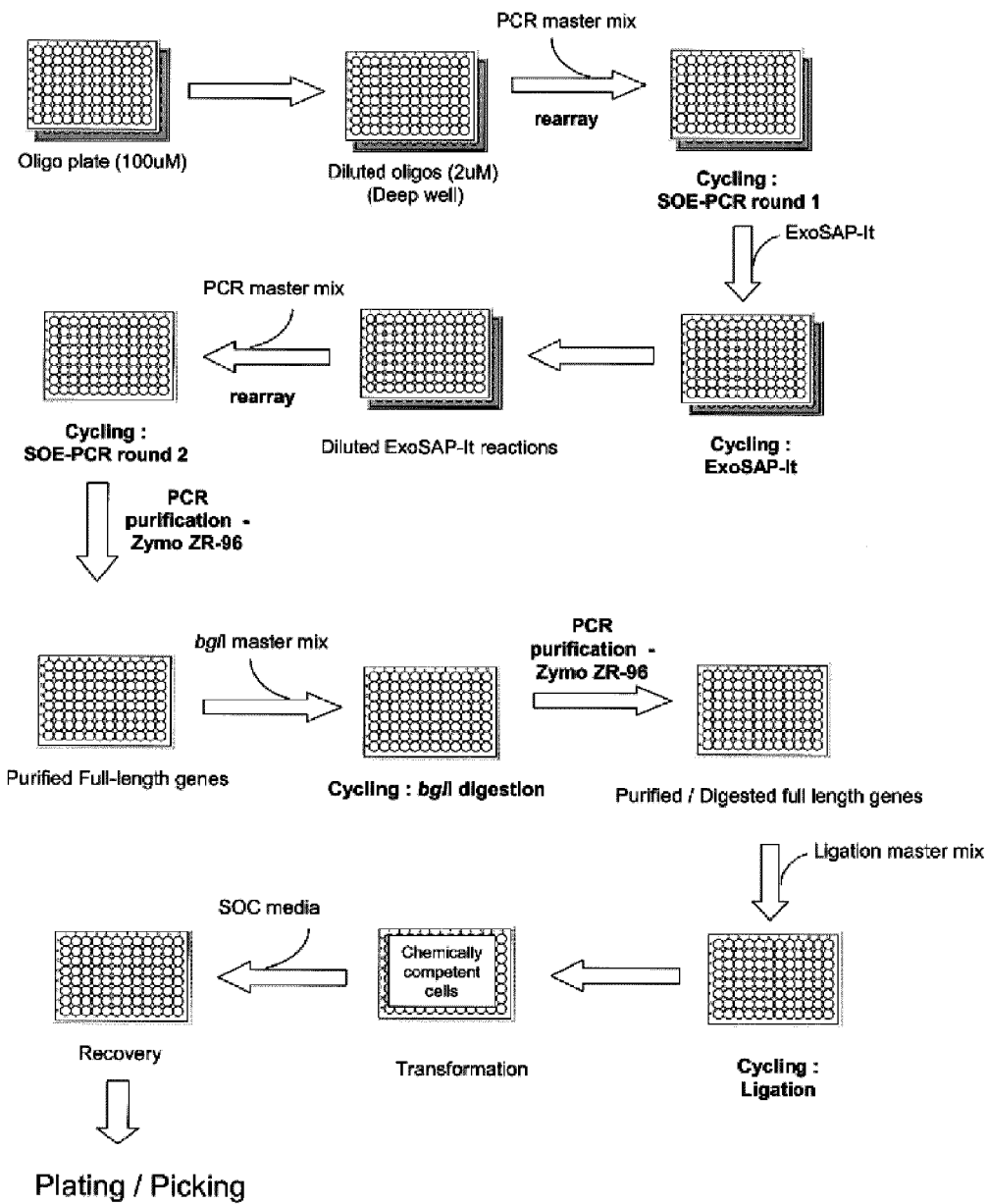

"Nucleobase" or "base" refers to those naturally occurring and synthetic heterocyclic moieties commonly known to those who utilize nucleic acid or polynucleotide technology or utilize polyamide or peptide nucleic acid technology to thereby generate polymers that can hybridize to polynucleotides in a sequence-specific manner. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine). Other non-limiting examples of suitable nucleobases include those nucleobases illustrated in FIGS. 2(A) and 2(B) of Buchardt et al. (WO 92/20702 or WO 92/20703).

"Nucleobase Polymer" or "Oligomer" refers to two or more nucleobases that are connected by linkages that permit the resultant nucleobase polymer or oligomer to hybridize to a polynucleotide having a complementary nucleobase sequence. Nucleobase polymers or oligomers include, but are not limited to, poly- and oligonucleotides (e.g., DNA and RNA polymers and oligomers), poly- and oligonucleotide analogs and poly- and oligonucleotide mimics, such as polyamide or peptide nucleic acids. Nucleobase polymers or oligomers can vary in size from a few nucleobases, from 2 to 40 nucleobases, to several hundred nucleobases, to several thousand nucleobases, or more.

"Operably linked" refers to a functional relationship between two or more nucleic acid (e.g., DNA) segments. In some embodiments, it refers to the functional relationship of a transcriptional regulatory sequence to a transcribed sequence. For example, a promoter (defined below) is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. In some embodiments, regulatory sequence is a translation regulatory sequence linked to a coding sequence.

"Overlapping region" refers to a region of a first polynucleotide that is complementary to a second polynucleotide, where the overlapping regions are capable of annealing to each other to form a hybridization complex. Generally, the first polynucleotide and the second polynucleotide will partially overlap such that the polynucleotides will have non-complementary regions that do not anneal between the two polynucleotides.

"Permutations" refers to the arrangement of elements (e.g., substitution mutations) from a given finite set. In the context of the descriptions herein for polypeptides and polynucleotides, differences in amino acid residues or nucleotide residues from a reference sequence, typically characterized as "mutations", can be arranged in various combinations in the sequence to form a permutation of the mutation set. Permutations include single mutations as well every combination of mutations possible from the defined set.

"Polynucleotides" or "Oligonucleotides" refer to nucleobase polymers or oligomers in which the nucleobases are connected by sugar phosphate linkages (sugar-phosphate backbone). Exemplary poly- and oligonucleotides include polymers of 2' deoxyribonucleotides (DNA) and polymers of ribonucleotides (RNA). A polynucleotide may be composed entirely of ribonucleotides, entirely of 2' deoxyribonucleotides or combinations thereof.

"Polynucleotide" or "Oligonucleotide Analog" refers to nucleobase polymers or oligomers in which the nucleobases are connected by a sugar phosphate backbone comprising one or more sugar phosphate analogs. Typical sugar phosphate analogs include, but are not limited to, sugar alkylphosphonates, sugar phosphoramidites, sugar alkyl- or substituted alkylphosphotriesters, sugar phosphorothioates, sugar phosphorodithioates, sugar phosphates and sugar phosphate analogs in which the sugar is other than 2'-deoxyribose or ribose, nucleobase polymers having positively charged sugar-guanidyl interlinkages such as those described in U.S. Pat. No. 6,013,785 and U.S. Pat. No. 5,696,253 (see also, Dagani 1995, Chem. Eng. News 4-5:1153; Dempey et al., 1995, J Am Chem Soc 117:6140-6141). Such positively charged analogues in which the sugar is 2'-deoxyribose are referred to as "DNGs," whereas those in which the sugar is ribose are referred to as "RNGs." Specifically included within the definition of poly- and oligonucleotide analogs are locked nucleic acids (LNAs; see, e.g. Elayadi et al., 2002, Biochemistry 41:9973-9981; Koshkin et al., 1998, J Am Chem Soc 120: 13252-3; Koshkin et al., 1998, Tetrahedron Letters 39:4381-4384; Jumar et al., 1998, Bioorganic & Medicinal Chemistry Letters 8:2219-2222; Singh and Wengel, 1998, Chem. Commun., 12:1247-1248; WO 00/56746; WO 02/28875; and, WO 01/48190; all of which are incorporated herein by reference in their entireties).

"Primers" refer to oligonucleotides having sequence complementary to a target sequence, generally referred to as a primer binding sequence. The complementary portion of a primer can be any length that supports specific and stable hybridization between the primer and the target sequence under the reaction conditions. The primers can be about 5 to 60 nucleotides long, about 10 to 35 nucleotides long, or can be from, and in particular, 10, 11, 12, 13, 14, 15, 16, 17, 18, 19, and/or 20 nucleotides long. Generally, primers for replication by polymerase are capable of supporting extension by the polymerase when the primer is annealed to the target sequence. "Amplification primer" refers to an oligonucleotide primer used for amplification of a target nucleic acid sequence.

"Forward primer" and "reverse primer" refer to a set of amplification primers, where one primer anneals to the 3' end of the target (template strand) while the other primer anneals to the 3' end of the complementary target strand to amplify an amplicon.

"Degenerate primer" as used herein refers to a primer that includes at least one degenerate codon at a position of a defined difference. Thus, although the term "degenerate primer" is singular it refers to a set of oligonucleotides having identical sequences except for at the position of a defined difference. Additionally, a "degenerate primer" as used herein can include more than one degenerate codon (e.g., NNT/VWG) and/or a mix of specific codons (e.g., TGG/TTC, or NNT/VWG/TGG) at the position of the defined difference. Degenerate primers can be used in PCR reactions to generate "degenerate amplicons" which can then be used to assemble and replicate "degenerate polynucleotide variants" according to the methods of the present disclosure (e.g., polynucleotide variants encoding a library of polypeptide variants having all 20 natural amino acids at each of several defined amino acid sequence positions.

"Proximate" refers to the nucleotide distance from a defined base (e.g., a first nucleotide mutation) to a second defined base (e.g., a second nucleotide mutation), where the first and second mutations can be accommodated in a single oligonucleotide primer used for amplification purposes (e.g., forward or reverse primer). Thus, in some embodiments, the term "proximate" is determined with respect to the length of the primer. In some embodiments, two mutations can be proximate if they are separated by 1, 2, 3, 4, 5, 6, 8, 10, 12, 14, 16, 18, 20, or 25 nucleotide bases and are within the primer. In some embodiments, the location of the mutations with respect to the 3' end of the primer is such that an oligonucleotide annealed to a template strand can undergo extension by polymerase, as described in detail below.

"Protein," "polypeptide," "oligopeptide," and "peptide" are used interchangeably to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Recombinant" when used with reference to, e.g., a cell, nucleic acid, polypeptide, expression cassette or vector, refers to a material, or a material corresponding to the natural or native form of the material, that has been modified by the introduction of a new moiety or alteration of an existing moiety by recombinant techniques, or is identical thereto but produced or derived from synthetic materials using recombinant techniques. For example, recombinant cells express genes that are not found within the native (non-recombinant) form of the cell (i.e., "exogenous nucleic acids") or express native genes that are otherwise expressed at a different level, typically, under-expressed or not expressed at all.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity.

"Replicating" refers to copying of a target polynucleotide sequence to synthesize a reverse complementary copy of the polynucleotide. Generally, replicating is done by polymerases that copy a template polynucleotide to synthesize a polynucleotide that is a reverse complement of the target polynucleotide sequence.

"Segment" refers to a sequence that is a portion of a larger polynucleotide sequence. The larger polynucleotide sequence can be divided into a plurality of segments, wherein the combination of the segments comprises the full length of the larger polynucleotide sequence.

"Polypeptide variant" or "polypeptide analog" as used herein refers to polypeptides which are comprised of a segment having functional activity, with or without retention of any improved property, and has substantial identity to a portion of a reference polypeptide. In some embodiments, analog polypeptides comprise a conservative or non-conservative amino acid substitution, or addition or deletion of one or more amino acid residues with respect to the reference sequence.

"Watson/Crick Base-Pairing" refers to a pattern of specific pairs of nucleobases and analogs that bind together through sequence-specific hydrogen-bonds, e.g., A pairs with T and U, and G pairs with C.

"Substitution" refers to the replacement of one or more nucleotides or amino acids by different nucleotides or amino acids, respectively, with respect to a reference sequence, such as, for example, a wild-type sequence.

"Substrate," "Support," "Solid Support," "Solid Carrier," or "Resin" are interchangeable terms and refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

"Array" refers to an arrangement of agents (e.g., proteins, antibodies, replicable genetic packages) on a substrate in positionally distinct locations. In some embodiments, the agents on the array are spatially encoded such that the identity of an agent can be determined from its location on the array. A "microarray" generally refers to an array in which detection requires the use of microscopic detection to detect complexes formed with agents on the substrate. A "location" on an array refers to a localized area on the array surface that includes agents, each defined so that it can be distinguished from adjacent locations (e.g., being positioned on the overall array, or having some detectable characteristic, that allows the location to be distinguished from other locations). The location can have any convenient shape (e.g., circular, rectangular, elliptical or wedge-shaped). The size or area of a location can vary significantly. Arrays may be constructed on substrates, such as glass or plastic microscope slides, and be configured in the form of wells, depressions, droplets, or other containers, or reaction vessels, such as a microplate well. In general, there is no restriction on the format of the array provided the individual sites to which the agents are disposed can be localized and identified.

"Reaction chamber" is meant the environment in which agents and/or reaction components takes place. Commercially available reaction vessels contain at least one reaction chamber, but can contain 8, 24, 96 or 384 reaction chambers. For the purposes of the present disclosure, "reaction chamber(s)," "well(s)," "reaction site(s)," are used interchangeably. An example of a reaction chamber is one of the 96 microtiter wells in a 96 well microtiter plate.

"Primer array" refers to the array of primers or primer sets used in an amplification reaction in positionally distinct locations on a substrate (e.g., array substrate). Generally, the primer set comprises a pair of forward and reverse primers used to amplify an amplicon.

"Amplicon array" refers to an arrangement of amplified polynucleotides in positionally distinct locations on a substrate (e.g., array substrate). In some embodiments, the amplicon array can have the same positional arrangement as the primer array, such as when the amplification reaction is carried out in the primer array to generate amplified polynucleotides.

"Plasmid", "vector", and "cassette" refer to an extra chromosomal element often carrying genes, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for expression of that gene in a host.

5.2 METHODS OF SYNTHESIZING POLYNUCLEOTIDE VARIANTS

The present disclosure provides methods of generating polynucleotide variants having a defined set of sequence differences from a reference polynucleotide sequence. In some embodiments, the methods are applicable for generating polynucleotides encoding polypeptide variants having defined differences in amino acid sequence as compared to a reference polypeptide. In some embodiments, the polynucleotide variants have a defined set of nucleotide differences in non-coding regions, e.g., silent mutations. The polynucleotides are efficiently generated by using libraries of polynucleotide fragments, where the members of the library encode one or more of the amino acid differences as compared to a reference polypeptide sequence, and the polynucleotide fragments are designed to have overlapping adjacent regions such that selection of an appropriate set of fragments, with and without mutations, allows their assembly into a polynucleotide variant, such as a polynucleotide encoding a desired polypeptide variant.

In some embodiments, the method for generating a polynucleotide encoding a polypeptide having an amino acid sequence with one or more defined differences in amino acid residues, comprises (a) selecting a plurality of defined amino acid residue differences relative to a reference amino acid sequence; (b) defining overlapping segments of a polynucleotide sequence encoding the polypeptide with the different amino acid sequence, or optionally the reference polypeptide, with each segment being bounded by a set of forward and reverse primer binding sequences, wherein a polynucleotide sequence difference encoding each of the plurality of amino acid residue differences is encompassed in the sequences of the forward and/or reverse primers that bind to the primer binding sequences; (c) amplifying each segment with the set of forward and reverse primers, wherein selected forward and/or reverse primer contain the polynucleotide sequence differences, to generate a library of amplicons comprising members encoding the defined amino acid differences and wherein the library comprises members sufficient for assembling two or more different amino acid sequence permutations of the defined amino acid residue differences; (d) assembling from the library a set of amplicons having complementary adjacent regions that together encode the polypeptide with a defined amino acid sequence permutation having one or more defined amino acid residue differences; and (e) replicating the set of assembled amplicons to synthesize the polynucleotide encoding the polypeptide. A library of amplicons containing all of the defined amino acid differences should allow the synthesis of a plurality of polynucleotides that encode for all possible permutations of amino acid sequences.

As will be apparent to the skilled artisan, selecting the plurality of defined amino acid residue differences can be obtained from various sources. In some embodiments, the amino acid residue positions and corresponding mutations for a defined polypeptide can be obtained from studies of random mutagenesis, such as that described in Crameri et al., 1998, "DNA shuffling of a family of genes from diverse species accelerates directed evolution," Nature 391:288-291; Crameri et al., 1997, "Molecular evolution of an arsenate detoxification pathway by DNA shuffling," Nature Biotech 15:436-438; Zhang et al., 1997, "Directed evolution of an effective fructosidase from a galactosidase by DNA shuffling and screening," Proc Natl Acad Sci USA 94:45-4-4509; Crameri et al., 1996, "Improved green fluorescent protein by molecular evolution using DNA shuffling, Nature Biotech 14:315-319; Stemmer, 1994, "Rapid evolution of a protein in vitro by DNA shuffling," Nature 370:389-391; Stemmer, 1994, "DNA shuffling by random fragmentation and reassembly: In vitro recombination for molecular evolution," Proc Natl Acad Sci USA 91:10747-10751; WO 95/22625; WO 97/0078; WO 97/35966; WO 98/27230; WO 00/42651; WO 01/75767 and U.S. Pat. No. 6,537,746. All publications are incorporated herein by reference.

Typically, a mutagenized library of polynucleotides is expressed and the expressed polypeptides screened for a desired property trait, and the mutations associated with the changes in the desired property identified. Large number of mutations affecting a polypeptide function can be readily obtained using these techniques.

In some embodiments, the choices of amino acid residue differences can be obtained from comparison of amino acid sequences of related proteins, such as those found in a sequence database. Sequence comparison can identify positions, for example conserved residues that may be important to protein function, which can then be targeted for defined amino acid changes. See, e.g., Wankhade et al., 2000, J. Biol. Chem. 275(38):29701-29708 and Reddy et al., 2001, Proteins: Structure, Function, and Genetics 42:148-163.

In some embodiments, the plurality of defined amino acid residue differences can be based on sequence differences found in nature, such as polymorphisms found for a particular gene. In some instances, the polymorphisms are associated with particular biological effects and associated phenotypes. See, e.g., Bidwell et al., 1999, Genes and Immunity 1:3-19; Chen et al., 2003, Mol. Biol. Evo. 18:1771-1788. Collections of polymorphisms can form the basis for defining a plurality of the amino acid residue differences for forming variant polypeptides of a reference amino acid sequence. Combinations of different amino acid polymorphisms can be used to examine the function of a particular protein.

When the plurality of amino acid residue differences is defined with respect to a reference sequence, the polynucleotide encoding the reference polypeptide or the polypeptide variants can be used as a basis for identifying segments for defining the amplicons to be generated to create the polynucleotide fragment (i.e., amplicon) library. In some embodiments, the polynucleotide sequence need not be restricted to any particular sequence as long as it encodes, or can be used as a basis to generate polynucleotides that encode, the amino acid sequence of interest. The polynucleotide can be based on the naturally occurring (e.g., wild-type) sequence or a sequence optimized for expression in a particular organism of interest (e.g., codon optimized). For example, if the polypeptide of interest is to be expressed in E. coli., a polynucleotide sequence in which the codons are optimized for expression in E. coli can be used. Codon optimization techniques are well within the skill of those in the art.

As will be apparent to the skilled artisan, dividing the polynucleotide into defined segments for amplification can be accomplished using techniques well known in the art. In some embodiments, since the segments are defined by primer binding sequences, which are themselves used to introduce mutations into the amplicon, division of the polynucleotide into segments can initially take into account the location of the mutations on the polynucleotide. The divisions of the polynucleotide into segments can also take into account the total length of the polynucleotide, the efficiency of replication (e.g., amplification of segments), and the desired number of amplicons for assembly. Other considerations will be apparent to the skilled artisan.

Amplification reactions can be affected by sequence, type of polymerase used, efficiency of primers, and unwanted side reactions (e.g., primer dimers). Thus, in some embodiments, depending on the total length of the polynucleotide to be assembled, the segment lengths can be 2000 bases or less, 1500 bases or less, 1200 bases or less, 1000 bases or less, 900 bases or less, 800 bases or less, 700 bases or less, 600 bases or less, 500 bases or less, 400 bases or less, 300 bases or less, 250 bases or less, or 200 bases or less to about 100 or as few as about 50 bases in length. Generally, length of the segments is from about 50 to about 1000 bases, about 200 to 1000 bases, about 300 to 700 bases, or about 400 to 600 bases, with about 500 bases being useful average length given the efficiency of polymerases used in amplification reactions. In various embodiments, the segments are overlapping such that the amplicons produced therefrom will also have overlapping adjacent regions (i.e., overlapping complementary regions) for assembling the polynucleotide.

In some embodiments, the adjacent overlapping regions should be of sufficient length and complementarity to permit the formation of stable annealed (i.e., hybridized) amplicons during assembly of the polynucleotide. Thus, in some embodiments, the length of overlap can be 4 or more nucleotides, 5 or more nucleotides, 6 or more nucleotides, 8 or more nucleotides, 10 or more nucleotides, 15 or more nucleotides, 20 or more nucleotides, 25 or more nucleotides, 30 or more nucleotides, 40 or more nucleotides, 50 or more nucleotides, and 100 or less, 90 or less, 80 or less, 70 or less, 60 or less nucleotides in length as permitted by the ability to form stable annealed amplicons. Since the overlap regions generally include the primer binding sequences use to generate the amplicons, the length of overlap can account for any differences in the sequence of the primer (e.g., forward and/or reverse) used to generate the polynucleotide differences encoding the mutation to be introduced.

In some embodiments, the segments are bounded by primer binding sequences to which the forward/reverse primers anneal. Where appropriate, the primer binding sequences that define the segments can also encompass the position of the polynucleotide that encodes an amino acid sequence difference. The primer binding sequence can be of any sufficient length to anneal to the primer (forward or reverse) during the amplification reaction. Accordingly the primer binding sequence can be 100 bases or less, 90 bases or less, 80 bases or less, 70 bases or less, 60 bases or less, 50 bases or less, 40 bases or less, 30 bases or less, 20 bases or less 15 bases or less, to about 8 bases or 10 bases. In some embodiments, the length of the primer binding sequences can comprise from about 8 to 50 bases, about 8 to 40 bases, about 10 to 30 bases, or about 15 to 25 bases. The primers typically can comprise lengths complementary to the primer binding sequences described above. Accordingly, in some embodiments, the length of the forward/reverse primers can be about 60 nucleotides or less, 50 nucleotides or less, 40 nucleotides or less, 30 nucleotides or less, 20 nucleotides or less 15 nucleotides or less, to about 10 nucleotides or even 8 nucleotides. In some embodiments, the length of the forward/reverse primers can be from about 8 to 50 nucleotides, about 8 to 40 nucleotides, about 10 to 30 nucleotides, or about 15 to 25 nucleotides.

Where the primer contains a sequence encoding a defined amino acid difference, the mutation can be located at a region of the primer that does not interfere with primer extension. In some embodiments, the mutation is located at about the middle of the mutagenic primer, where the primer has a Tm that is sufficient to anneal to the template nucleic acid and serve as a primer for the polymerase mediated extension reaction. In some embodiments, the polynucleotide sequence differences can be located, depending on the length of the primer, about 5 bases, 6 bases, 8 bases, 10 bases, 12 bases, 15 bases, 20 bases, 25 bases from the 3' end of the primer. Accordingly, in some embodiments the length of the forward/reverse primers can be from about 8 to 50 nucleotides, about 8 to 40 nucleotides, about 10 to 30 nucleotides, or about 15 to 25 nucleotides, and further comprise nucleotide sequence difference at about the middle of the primer. Thus, in some embodiments the forward/reverse primers are about 50 nucleotides in length with a nucleotide difference about 25 nucleotides from the 3' end, about 40 nucleotides in length with a nucleotide difference about 20 nucleotides from the 3' end, about 30 nucleotides in length with a nucleotide difference about 15 nucleotides from the 3' end, about 25 nucleotides in length with a nucleotide difference about 12 nucleotides from the 3' end, or about 20 nucleotides in length with a nucleotide difference about 10 nucleotides from the 3' end, The stability of the oligonucleotide primers, e.g., the thermal melting temperature, is a function of ion strength, temperature, G/C content, and the presence of chaotropic agents and can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad. Sci. USA 83:8893-8897; Freier et al., 1986, Proc. Natl. Acad. Sci. USA 83:9373-9377; Kierzek et al., Biochemistry 25:7840-7846; Rychlik et al., 1990, Nucleic Acids Res 18:6409-6412 (erratum, 1991, Nucleic Acids Res 19:698); Sambrook et al., 2001, Molecular Cloning: A Laboratory Manual, 3rd Ed., Cold Spring Harbor Laboratory Press, NY; Suggs et al., 1981, In Developmental Biology Using Purified Genes (Brown et al., eds.), pp. 683-693, Academic Press; and Wetmur, 1991, Crit. Rev Biochem Mol Biol 26:227-259. All publications incorporate herein by reference).

To generate the library of amplicons, forward and reverse primers that anneal to the primer binding sequences of each segment of the polynucleotide are used in an amplification reaction to generate amplicons. Where the amplicon has a polynucleotide difference encoding a defined amino acid change relative to the reference sequence, the sequence of the forward and/or reverse primers are designed to introduce the different sequence (i.e., mutation) in the amplification reaction. Suitable combinations of forward and reverse primers are used to generate a library of amplicons comprising members that can encode for each of the plurality of amino acid residue differences.

In some embodiments, the sets of forward and reverse primers can be stored in an array, for example a primer array, such that they can be easily accessed when amplicons are needed for synthesis of a polynucleotide encoding a defined amino acid sequence permutation. As will be appreciated in the art, the oligonucleotide primers can be used to introduce any type of mutation selected in the defined plurality of amino acid residue differences, including, among others, amino acid insertions, deletions, and substitutions. The substitutions can be conservative or non-conservative mutations, as dictated by the chosen plurality of amino acid residue differences.

One advantage of the methods of synthesizing a plurality of polynucleotide variants disclosed herein is that they can provide very large libraries of highly diverse yet well-defined nucleotide differences that allow more efficient exploration of sequence diversity space. For example, large libraries may be generated wherein each variant has only a single defined nucleotide difference. Such libraries provide a broad survey of sequence diversity that can be screened and analyzed with greater confidence that the structure-function relationships identified are accurate (e.g., fewer false positives and false negatives). The ability of the methods to generate large libraries of polynucleotide variant sequences with high accuracy (e.g., 75%, 85%, 95% or greater of correct full-length sequences) greatly enhances the advantages of generating and analyzing such libraries. Thus, in some embodiments the plurality of polynucleotide variants synthesized using the methods can comprise at least 10, 20, 30, 40, 50, 100, 200, or more different polynucleotide variants, wherein each variant comprises a different defined nucleotide difference at one of 10, 20, 30, 40, 50, 100, 200, or more different selected positions (i.e., 10, 20, 30, 40, 50, 100, 200, or more distinct single site mutants).

In some embodiments, more than one amino acid sequence difference can be present on the same amino acid residue position in a polypeptide sequence. In these embodiments, different amplicons from the same overlapping segment can be generated, where each amplicon is prepared with forward and reverse primer pairs for each defined mutation at the identical residue position. To prepare a polynucleotide encoding a particular sequence permutation at that specific amino acid residue position, one of the amplicons containing the desired mutation (i.e., defined nucleotide difference) is chosen and assembled as a member of the set of amplicons to generate the polynucleotide encoding a polypeptide containing the desired mutation(s) at the specified amino acid residue position.

In some embodiments, more than one pair of primers (e.g., a set of degenerate primers) can be used to generate a set of amplicons (i.e., polynucleotide fragments) that can be used to assemble a set of polynucleotide variants encoding polypeptides having more amino acid residue changes (e.g., substitutions) at a specific defined position. The polynucleotide variants assembled from the amplicons made using degenerate primers can be sequenced before or after their encoded polypeptide is assayed in order to determine the specific sequence at the position of interest.

In some embodiments, a plurality of degenerate primers (e.g., each primer having a different codon at a selected position for mutation) can be separately amplified (e.g., a Round 1 reaction) to generate a plurality of "degenerate amplicons." Each separate well (or "pool") of degenerate amplicons so generated comprises a plurality of different amplicons with identical sequences except at the position of defined difference(s) that are defined by the sequences of the degenerate primers used. These degenerate amplicons (having a plurality of defined nucleotide differences at one or more positions) can then be separately assembled with one or more overlapping amplicons (either "homogenous" amplicons or pools of degenerate amplicons) and replicated (e.g., in a Round 2 SOE-PCR reaction) to yield separate well of full-length "degenerate polynucleotide variants," wherein the polynucleotide variants comprise variant sequences comprising all of the defined differences designed in the degenerate amplicons used in the first step.

For example, degenerate primers can be designed having defined nucleotide differences comprising degenerate codons (e.g., NNK, or the 23 codon set of NNT, VWG, and TGG) representing 20 amino acids at 3 positions in an encoded polypeptide. These degenerate primers can be used with reference polynucleotide template in 6 separate Round 1 PCR reactions to generate 6 pools of degenerate amplicons (i.e., one pair of overlapping degenerate amplicons for each of the 3 positions of defined nucleotide difference). Separately assembling and replicating each of the three pairs of overlapping degenerate amplicons in 3 separate Round 2 SOE-PCR reaction results in 3 separate pools of full-length polynucleotide variants each pool containing polynucleotides encoding a set of degenerate polypeptide variants having all 20 different amino acids at each of the 3 selected positions targeted for mutation. Although the 3 separate pools can be maintained as an addressable library of polynucleotide variants with 3 members having full degeneracy at each of 3 selected positions, surprising advantages of efficiency in transformation and screening can be realized (particularly with larger libraries) by destroying the addressability and combining all 3 members of the library in a single pool. Accordingly, the 3 pools of degenerate polynucleotide variants are combined resulting in a pooled library of polynucleotide encoding 60 polypeptides comprising all possible amino acids at each of the three targeted positions. This pooled library comprises a well-defined set polynucleotide variants encoding complete amino acid sequence diversity (e.g., saturation mutagenesis) at 3 targeted positions. The pooled library can then be cloned into an expression system, transformed in a single reaction, plated, picked and screened. Since the synthesis method involving the Round 1 and Round 2 steps results in a high level of accuracy (e.g., 75%, 85%, 95%, or greater of the desired full-length variants) a relatively low number of colonies can be picked and screened to access 75%, 85%, 95%, 99% or even greater screening coverage of the library of polypeptide variants.

As will be apparent to the skilled artisan, in some embodiments, the methods employing degenerate primers (and the resulting degenerate amplicons) can be used to prepare polynucleotide variants having defined differences at every position. In some embodiments, it is contemplated that the method is used to provide "saturation mutagenesis" libraries wherein each polynucleotide variant member has a different sequence comprising one of 23 different codons at a different selected position of the reference polynucleotide sequence. Thus, in some embodiments the methods are capable of providing a plurality of polynucleotide variants comprising at least 23, 46, 69, 92, 115, 230, 460, 920 or more different polynucleotide variants each comprising one of 23 different codons at one of 1, 2, 3, 4, 5, 10, 20, 40, or more different selected positions. The ordinary artisan will recognize that in other embodiments, more or fewer codons can be used at positions of defined nucleotide differences and/or multiple selected positions in each variant can be mutated using the methods disclosed herein.

The present disclosure also provides in some embodiments that the overall number of variants can be controlled by mixing more or less degeneracy in the primers at different positions of defined differences. Thus, the method allows full saturation mutagenesis to be carried out at one or more selected positions while single defined differences or smaller subsets of degeneracy are introduced at other selected positions of the polynucleotide. For example, in the same reference polynucleotide sequence comprising defined differences at three positions, at the first selected position for mutation there may be only 1 defined difference (e.g., G changed to T), at the second selected position there may be a degenerate codon encoding 15 different amino acids (e.g., NNT), and at the third selected position there may be two degenerate codons and a specific codon used representing 23 codons encoding 20 amino acids (e.g., NNT, VWG, and TGG).

In some circumstances, it can be useful to generate a library of polynucleotides variants comprising diverse permutations of multiple nucleotide differences at a set of selected positions. Accordingly, in some embodiments of the disclosure, a method of synthesizing polynucleotide variants can be carried out wherein the Round 1 PCR step employs a mixture of mutagenic primers, comprising a defined difference at a selected position, and non-mutagenic primers, comprising no difference at the selected position (i.e., the same sequence at the selected position as the reference polynucleotide). By using a mixture of mutagenic to non-mutagenic primers having a defined ratio in the Round 1 PCR amplification, the resulting amplicons comprise a mixture of sequences with or without the defined difference at the targeted position. By assembling and replicating this mixture of amplicons in a pooled Round 2 SOE-PCR reaction, a library of polynucleotide variants is generated having a stochastic mix of the defined nucleotide differences at the set of selected positions. For example, with 1 defined difference (e.g., 1 specific codon substitution) designed at each of 13 targeted positions and a 1:2 ratio of mutagenic to non-mutagenic primers, the resulting pool of polynucleotide variants comprises a stochastic mix of polynucleotides having from 0 to 13 of the defined differences. This embodiment of the methods disclosed herein thus provides a fast and easy way to generate combinatorial libraries of polynucleotide variants with combinations of defined differences at targeted positions.

In one embodiment of this method for generating combinatorial libraries, the plurality of primer mixtures are separately amplified in a plurality of Round 1 PCR reactions to generate a plurality of pools of amplicons having overlapping regions (e.g., N+1 pools of amplicons for N targeted positions when one defined difference is included per primer). The plurality of pools of amplicons so generated is then combined in a single Round 2 SOE-PCR reaction. The resulting pool of polynucleotide variants comprises a stochastic mix of the defined differences (e.g., nucleotide changes encoding amino acid changes) at the targeted positions.

Alternatively, the plurality of primer mixtures can be combined and amplified in a single Round 1 PCR reaction to generate a single pool of mixed amplicons. No further mixing of the amplicons is necessary, and the Round 2 SOE-PCR assembly and replication of the amplicons is carried out to generate the pool comprising the stochastic mix of polynucleotide variants.

As will be apparent to the skilled artisan, in some embodiments, an overlapping segment defined for a polynucleotide sequence may not have any associated mutations. Additionally, the same segment may in one amino acid sequence permutation encompass a specified mutation, but in some sequence permutations may not have any mutation associated with the segment. Thus, in some embodiments, the library of amplicons can contain members that do not have any polynucleotide sequence differences as compared to the reference sequence for a particular segment. These bridging polynucleotides, which have no associated changes in sequence as compared to the reference sequence, can be used as a connector to assemble the complete polynucleotide.

With the appropriate choice of segments, the amplicon library comprises members that can be used to assemble at least two or more different amino acid sequence permutations of the defined amino acid differences relative to the reference sequence. For example, a plurality of mutations defined by amino acid residue differences A and B can have the following permutations: A alone, B alone, or A and B. Thus the amplicon library has sufficient members to generate an amino acid sequence permutation having independently an A mutation or B mutation. In some embodiments, the amplicon library has members sufficient to generate every amino acid sequence permutation of the defined amino acid residue differences relative to the reference sequence. Thus, for the given example, the amplicon library has sufficient members to generate amino acid sequence permutations having independently an A mutation or B mutation, or an A+B mutation. Since the size of the amplicons will correspond to the size of the segments, the amplicons can be 2000 bases or less, 1500 bases or less, 1200 bases or less, 1000 bases or less, 900 bases or less, 800 bases or less, 700 bases or less, 600 bases or less, 500 bases or less, 400 bases or less, 300 bases or less, 250 bases or less, or 200 bases or less to about 100, or as few as about 50 bases in length. Generally, length of the amplicons is from about 50 to about 1000 bases, about 200 to 1000 bases, about 300 to 700 bases, or about 400 to 600 bases, with about 500 bases or less a useful length given the efficiency of polymerases used in amplification reactions. In some embodiments, the amplicons are about 400 bases or less in length.

Generally, the amplification reaction can use any enzyme used for polymerase mediated extension reactions, such as Taxi polymerase, Pfu polymerase, Pwo polymerase, Tfl polymerase, rTth polymerase, Tli polymerase, Tma polymerases, and Klenow fragment. Conditions for amplifying a polynucleotide segment using polymerase chain reaction can follow standard conditions known in the art. See, e.g., Sambrook et al., 2001, Molecular Cloning: A Laboratory Manual, 3rd Ed., Cold Spring Harbor Laboratory Press, NY and Ausubel et al., 1989, Current Protocols in Molecular Biology, Greene Publishing Associates and Wiley Interscience, N.Y. (updates up to 2008); references incorporated herein by reference.

In some embodiments, amplification of each amplicon can be carried out in separate reactions, thereby minimizing the need to isolate one amplicon product from another amplicon. However, the amplification reactions for two or more amplicons can be carried out in a single reaction and the products isolated, such as by electrophoresis or chromatography. In some embodiments, the products of the amplification reaction can be treated with various combinations of exonucleases and phosphatases to remove remaining primers and free nucleotides (e.g., combination of exonuclease I and alkaline phosphatase).

To generate the polynucleotide encoding the polypeptide with the defined amino acid sequence permutation, a set of amplicons having complementary overlapping regions is selected and assembled under conditions that permit the annealing of the complementary overlapping regions to each other. For example, the amplicons can be denatured and then allowed to anneal to form a complex of amplicons that together encode the polypeptide with a defined amino acid sequence permutation having one or more of the amino acid residue differences relative to a reference sequence. Generally, assembly of each set of amplicons can be carried out separately such that the polynucleotide encoding one amino acid sequence permutation is readily distinguished from another polynucleotide encoding a different amino acid sequence permutation. In some embodiments the assembly can be carried out in addressable locations on a substrate (e.g., an array) such that a plurality of polynucleotides encoding a plurality of defined amino acid sequence permutations can be generated simultaneously.

In some embodiments, assemblies can be prepared such that multiple (i.e., 2 or more) amplicons are represented for the same fragment. The resulting product from this assembly reaction will contain a mixture of polynucleotides containing different permutations of the defined amino acid sequence differences. This mixture can be cloned directly and variants can be sequenced before or after encoded polypeptides are assayed.

The assembled amplicons is replicated using a polymerase to synthesize the polynucleotide encoding the polypeptide of interest. In some embodiments, the reaction conditions can use the same conditions and polymerases used for the amplification reaction. The assembled amplicons act as primers such that a single round of replication creates a duplicate of the assembled amplicons. Generally, in the replicating step, primers that anneal to primer binding sequences that flank the polynucleotide (i.e., terminal 5' region and terminal 3' region) can be added to amplify the polynucleotide product by carrying out additional amplification reactions. In some embodiments, these flanking primers can incorporate recognition sequences for restriction enzymes to ease cloning of the synthesized polynucleotide product into plasmids or vectors, such as expression vectors.

In some embodiments, the flanking primers can have sequences that allow for direct in vitro expression using a coupled transcription-translation systems for synthesis of the protein product without the need for transformation into a host organism. Hence, some flanking primers can incorporate control sequences to control the expression of the polypeptide coding region. Amplification reactions using such flanking primers can operably link the control sequences to the polypeptide coding region of interest.

In some embodiments, the plurality of amino acid differences is at least 2. In some embodiments, the plurality of amino acid differences is at least 2, 3, 4, 5, 6, 7, 8, 9, 10, 11, 12, 13, 14, 15, or more. Accordingly, the number of defined nucleotide differences can range from 2 to 45, or more. The number of permutations for "n" plurality of defined amino acid residue difference is given by the formula n!/(k!(n−k)!, where n is the number of non-mutually exclusive mutations and k is the number of amino acid differences and n! denotes the factorial operator. In some embodiments, the size of the amplicon library, for example for a minimum of 2 amino acid residue differences is a library size containing at least 3 different amplicons. In some embodiments, the size of the library is at least 5, 6, 7, 8, 9, 10, 11, or even more different amplicons. For example, for a plurality of variants comprising at least 10 defined differences, assuming none of the differences are located proximately such that more than 1 can be included per primer, assembling variants with 10 defined differences uses up to 11 amplicons per assembly reaction. Assuming a plurality of different mutations are desired at any of the plurality of positions having defined differences, much larger libraries of amplicons can be used. Accordingly, in some embodiments, the library of amplicons can comprise is at least 5, 10, 20, 30, 40, 50, 75, 100, or more different amplicons.

Once the library of amplicons have been synthesized, any polynucleotide encoding a specified amino acid sequence permutation based on a plurality of amino acid residue difference can be made using the library of amplicons. In some embodiments, the method of generating a polynucleotide encoding a polypeptide having an amino acid sequence with one or more defined differences in amino acid residues as compared to a reference polypeptide sequence can comprise the steps of: (a) assembling a set of amplicons having complementary overlapping adjacent regions, where the assembled set of amplicons comprise a polynucleotide sequence encoding an amino acid sequence with one or more defined amino acid residue difference as compared to a reference sequence, where the amplicons are selected from a library of amplicons having members encoding a plurality of amino acid differences, and (b) replicating the set of assembled overlapping polynucleotide fragments to synthesize the polynucleotide of interest.

In some embodiments, the amplicon library can be used to generate polynucleotides encoding any permutation of a defined plurality of defined amino acid differences, the method comprising: (a) generating permutations of amino acid sequences differing from a reference amino acid sequence based on a plurality of defined amino acid residue differences as compared to a reference amino acid sequence, (b) selecting a defined amino acid sequence permutation and determining a corresponding polynucleotide sequence based on a reference sequence, (c) selecting a set of overlapping polynucleotide fragments encoding the defined amino acid sequence permutations, where at least each overlapping polynucleotide fragment encoding an amino acid difference is from a plurality of polynucleotide fragments encoding different known amino acid residue differences, wherein the plurality of fragments has members sufficient to assemble polynucleotides encoding at least two different amino acid sequence permutations, (d) assembling the set of polynucleotide fragments having complementary overlapping adjacent regions, and (e) replicating the set of assembled overlapping fragments to synthesize the polynucleotide encoding the polypeptide. For each desired amino acid sequence permutation, the steps of (b) to (e) can be repeated.

Figure 4:
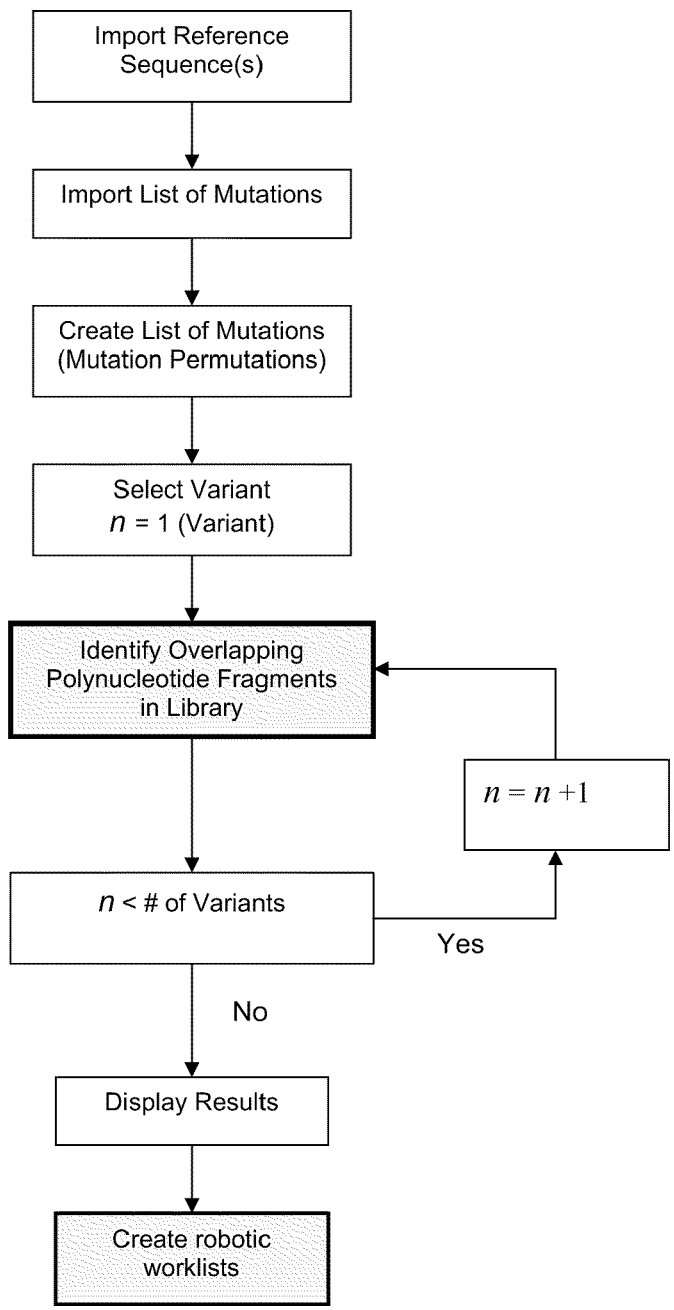
FIG. 4 shows a flowchart for generating polynucleotides encoding variants by use of library of overlapping polynucleotide fragments.

An exemplary process for generating the amplicons for "n" number of variants is shown in FIG. 4. In the illustrated embodiment, the process comprises: (a) importing a reference sequence and a list of mutations associated with the sequence, (b) creating a list of permutations based on the list of mutations, (c) selecting a defined permutation of the amino acid sequence (i.e., variant 1), (d) identifying overlapping polynucleotide fragments from a library of amplicons (e.g., as prepared in FIG. 5), (e) determining the number of variants and if the number of variants is less than the total number of desired variants, reiterating steps (a) to (d).

For efficient synthesis of the amplicon libraries, appropriately designed oligonucleotide primers are used in an amplification reaction. In some embodiments, the method of generating a library of overlapping polynucleotide fragments can comprise: (a) generating a plurality of permutations of amino acid sequences differing from a reference amino acid sequence based on a plurality of defined amino acid residue differences from a reference amino acid sequence, and for each permutation (i) determining a polynucleotide sequence encoding the amino acid sequence based on a reference polynucleotide sequence; (ii) scanning a polynucleotide sequence and identifying a change in polynucleotide sequence encoding an amino acid residue difference, and optionally determining the proximity of a next change in polynucleotide sequence encoding a next amino acid residue difference in the amino acid sequence permutation; (iii) selecting a forward oligonucleotide primer having a sequence encoding the amino acid difference, and optionally including the next change in polynucleotide sequence in the same forward primer if proximate to the change in polynucleotide sequence; (iv) scanning a polynucleotide sequence from the location of the forward primer until the next change in polynucleotide sequence is identified or until the end of the polynucleotide, and selecting a reverse oligonucleotide primer for amplifying a polynucleotide fragment with the forward oligonucleotide primer, wherein the reverse primer has a sequence that optionally encodes the next change in amino acid residue difference; (v) reiterating steps (ii) to (iv) for each change in polynucleotide sequence encoding an amino acid residue difference until all changes in polynucleotide sequence are present on oligonucleotide primers and ends of the polynucleotide sequence is reached; and (g) amplifying with each set of forward and reverse oligonucleotide primers to generate the library of overlapping amplicons having members encoding the amino acid differences. In these embodiments, when scanning of the polynucleotide sequence encounters the end of the polynucleotide, flanking primers can be used in combination with the internal primers to complete the generation of the amplicons.

Figure 5:
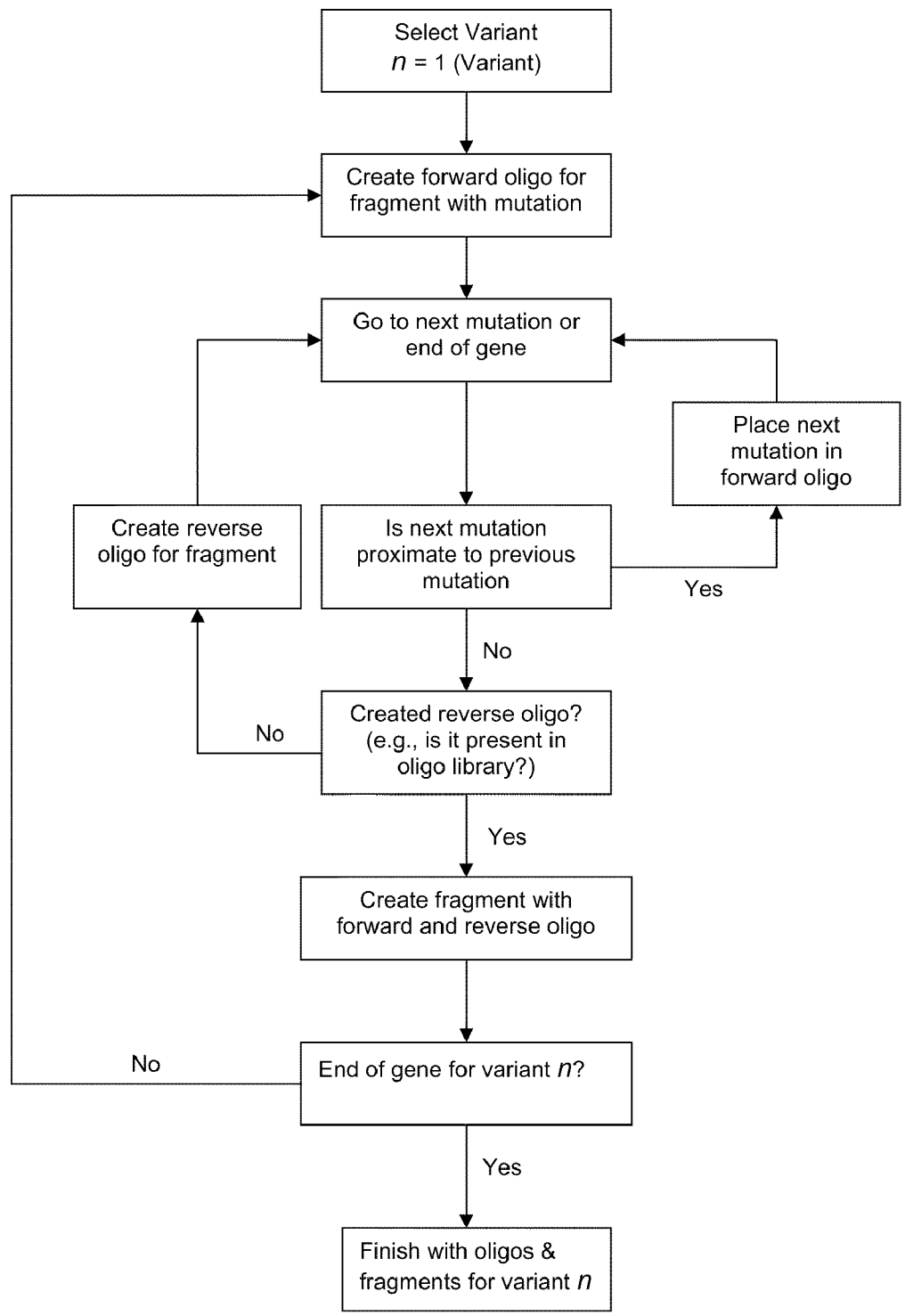
FIG. 5 shows a flowchart for generating a library of oligonucleotide primers for generating a library of overlapping polynucleotide amplicons for each amino acid sequence permutation.

An exemplary process for selecting the appropriate forward and reverse primers is illustrated in FIG. 5. In FIG. 5, the process for selecting the oligonucleotide primers comprises: (a) selecting a variant (an amino acid sequence permutation) and generating its corresponding polynucleotide sequence based on a reference sequence, (b) creating a forward oligonucleotide primer for a fragment with a first mutation, (c) scanning the sequence from the first mutation to the next mutation or to the end of the gene and creating a reverse oligonucleotide primer for the next mutation, (d) and if the next mutation is proximate to the first mutation, placing the next mutation in the same forward oligonucleotide primer, (e) reiterating steps (b) to (d) until ends of polynucleotide variant n is reached.

As noted above, in some embodiments where the polynucleotide has been separated out into overlapping segments defined by a set of forward and reverse primers, the forward and reverse primers may have no associated mutations. One context in which this may occur is if the polynucleotide segments are to be restricted in size, for example about less than 1000 bases, because of a need for efficient synthesis of an amplicon, such that not all the segments have defined changes in polynucleotide sequence. In some embodiments, in preparing the oligonucleotides based on the method above, the search of the sequence can be limited to a particular size "1", for example by about 1200 bases in step (iv) for selecting a reverse primer. In other words, following the identification of a forward primer based on a sequence difference, a scan is made in one or the other direction of the polynucleotide sequence to determine the nucleotide distance to the next mutation. If the distance exceeds the set limit, a segment that does not encompass any mutations can be created to bridge two segments that contain the two distant mutations. The scanning process can be reiterated at the point of the next mutation.

As noted above, the oligonucleotide primers, either alone or in sets (e.g., forward and reverse oligonucleotides) as well as the corresponding amplicons can be placed on addressable substrates for automation and/or storage. Oligonucleotide primers in the addressable substrates, also described herein as primer array, can be robotically accessed to synthesize any libraries of amplicons for a defined plurality of amino acid differences. Likewise, the amplicons in the addressable substrates, also described herein as amplicon arrays, can be accessed to generate a polynucleotide sequence encoding a desired amino acid sequence permutation based on the defined plurality of amino acid residue differences. A substrate or solid support for the array can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments. In some embodiments, the substrate is a reaction chamber. Commercially available reaction vessels contain at least one reaction chamber, but can contain 8, 24, 96 or 384 reaction chambers. An example of a reaction chamber is one of the 96 microtiter wells in a 96 well microtiter plate.

In some embodiments, a robotic system and an associated computer system capable of sampling primers or primer pairs from the arrays can be used to deliver them to a reaction chamber. Reagents for polymerase mediated amplification can also be delivered to each set of primers in the reaction chamber followed by implementation of an amplification routine (such as in a automated thermocycler). This allows formation of an addressable substrate containing defined amplicons based on overlapping segments of a polynucleotide sequence. The robotic system can choose the appropriate set of amplicons based on the desired permutation of the amino acid sequence, the flanking primers for amplification of the final polynucleotide product, and deliver the reagents for the assembly and amplification reaction. An exemplary robotic system is provided in FIG. 6. The robotic system in FIG. 6 comprises instructions for (a) selecting a segment and associated amplicon for amplification, (b) identifying forward and reverse oligonucleotides for the selected fragment (i.e., amplicon), storing data information on the oligonucleotides on list of unique oligonucleotides (e.g., 96 well microtiter plate), and placing the oligonucleotides on a first addressable substrate (c) storing data information on synthesized fragment (e.g., position on array, sequence, oligonucleotides used, etc) to list of unique fragments, and placing the oligonucleotide on a second addressable substrate, (d) determining the number of fragments selected against the total number of fragments required for assembly, and reiterating steps (a) to (d) until all fragments have been selected, (e) placing the assembled gene into a third addressable substrate, and reiterating steps (a) to (d) until all desired variants have been generated.

In some embodiments, the present disclosure also provides libraries of polynucleotide fragments (i.e., amplicons) for assembling a plurality of polynucleotides encoding different amino acid sequence permutations. In some embodiments, the plurality of polynucleotides comprises: polynucleotide fragments with overlapping adjacent regions, each polynucleotide fragment being bounded by primer binding sequences for forward and reverse primers, wherein the plurality of polynucleotides have members that encode in the primer binding sequences of a specific amino acid residue difference from a defined plurality of amino acid residue differences relative to a reference amino acid sequence such that the plurality of polynucleotide fragments encode all of a selected plurality of amino acid residues differences from the defined plurality of amino acid residue differences; and wherein the plurality of polynucleotide fragment comprises members for assembling two or more different amino acid sequence permutations of the defined amino acid differences. In some embodiments, the plurality of polynucleotide fragments comprises members sufficient for assembling all of the possible amino acid sequence permutations of the selected plurality of amino acid residue differences. In some embodiments, the members of the plurality are amplicons formed using the forward and reverse primers.

As will be apparent to the skilled the artisan, the methods described herein can be practiced using standard techniques available to the skilled artisan, such as that described in Sambrook et al., 2001, Molecular Cloning: A Laboratory Manual, 3rd Ed., Cold Spring Harbor Laboratory Press, NY and Ausubel et al., 1989, Current Protocols in Molecular Biology, Greene Publishing Associates and Wiley Interscience, N.Y. (updates up to 2008). Oligonucleotides can be synthesized using known chemical methodologies, such as those based on phosphoramidite solid phase synthesis methodologies (See, e.g., Wright, et al., 1993, Tetrahedron Letters 34, 3373-3376; Caruthers, 1991, Acc. Chem. Res. 24, 278-284; and references cited herein).

Also provided herein are computer implemented systems in the form of computer software for carrying out the methods described above. In some embodiments, the computer program product comprises a machine readable storage medium having program instructions comprising codes for each of the steps of: (a) importing a reference sequence and a list of mutations associated with the sequence, (b) creating list of permutations based on the list of mutations, (c) selecting a defined permutation of the amino acid sequence, (d) identifying overlapping polynucleotide fragments from a library of amplicons (e.g., as prepared in FIG. 5), (e) determining the number of variants and if the number of variants is less than the total number of desired variants, reiterating steps (a) to (d).

In some embodiments, the computer program product comprises a machine readable storage medium having program instructions comprising codes for each of the steps of: (a) selecting a variant (an amino acid sequence permutation) and generating its corresponding polynucleotide sequence based on a reference sequence, (b) creating a forward oligonucleotide primer for a fragment with a first mutation, (c) scanning the sequence from the first mutation to the next mutation or to the end of the gene and creating a reverse oligonucleotide primer for the next mutation, (d) and if the next mutation is proximate to the first mutation, placing the next mutation on the same forward oligonucleotide, (e) reiterating steps (b) to (d) until ends of polynucleotide variant n is reached.

Figure 6:
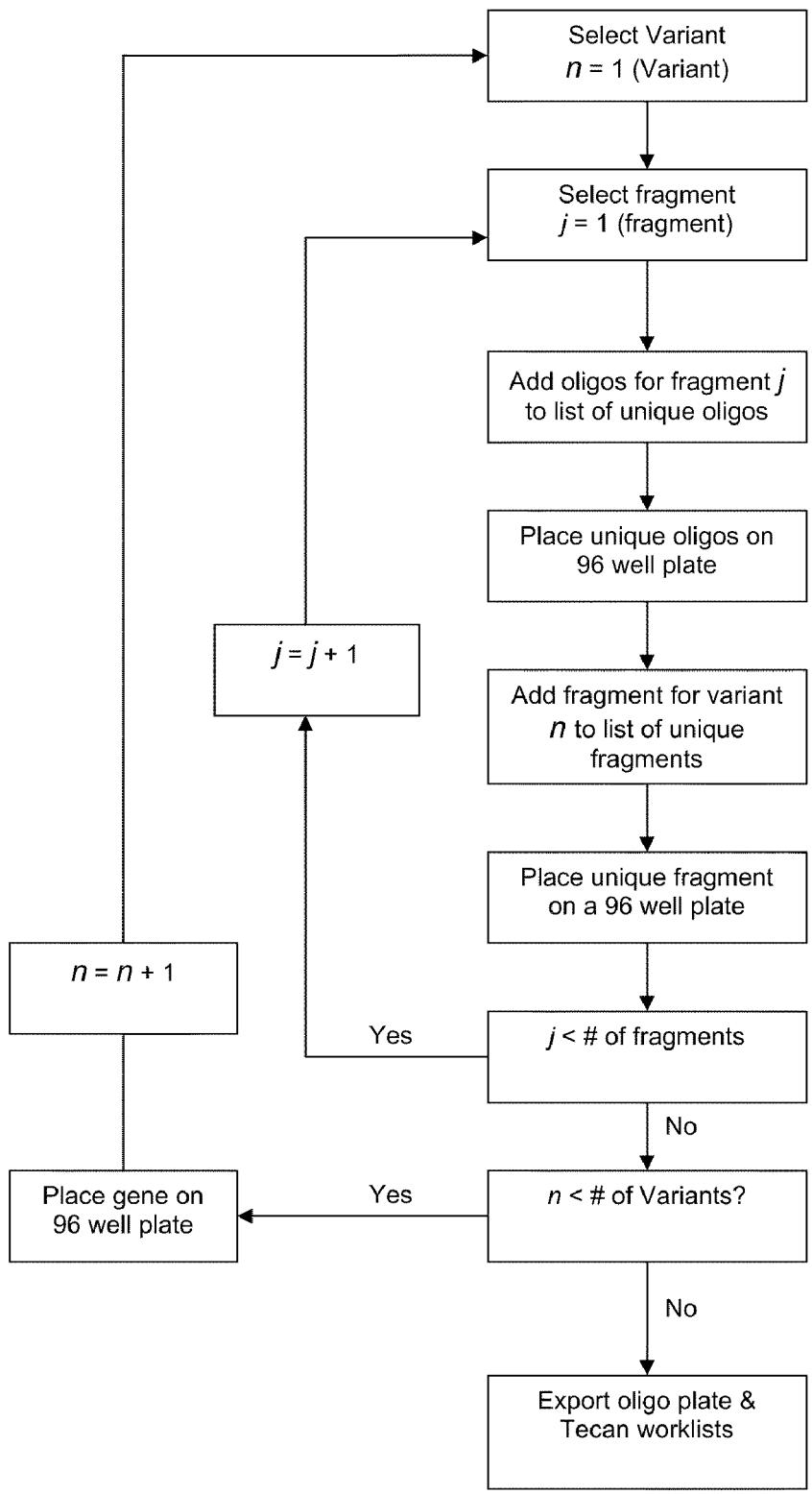
FIG. 6 shows a flowchart of instructions for automated creation and selection of oligonucleotide primers and overlapping oligonucleotide fragments.

As shown in the illustrations of FIG. 4, FIG. 5, and FIG. 6, the computer implemented programs for selection of the amplicons, selection of oligonucleotide primers, and storage in addressable formats can be integrated to permit automation of various steps of the methods of the disclosure.

As described herein, in some embodiments, the method can be used to synthesize polynucleotides encoding polypeptides having a defined set of mutations selected from a plurality of defined differences in amino acid residues from a reference sequence. The methods herein allow efficient synthesis of various permutations of amino acid sequences based on the amino acid residue differences. Efficient synthesis of polynucleotides encoding various amino acid sequence permutations is useful for a variety protein engineering applications. See, e.g., US application publication US20060195947; US application publication. US20050153417; and U.S. Pat. No. 7,220,566. In some embodiments, the methods can be use to synthesize polynucleotides encoding enzyme variants having improved properties based on a set of mutations known to affect different properties of the enzyme. For example, some mutations can affect, among others, enzyme activity, thermal stability, substrate specificity, stereoselectivity, stereospecificity, and refractoriness to product inhibition. While traditional techniques of random mutagenesis and protein evolution techniques can lead to identification of mutations affecting these various enzyme properties, many of these mutations can occur independently of the others. Using the methods herein, various permutations of mutations affecting different traits, such as enzyme activity, substrate specificity, and thermal stability can be made and screened to identify engineered enzymes having desired multiple altered traits.

The methods provided herein provide surprising efficiency and accuracy in generating large libraries of polynucleotide variants comprising various permutations of sequence changes. For example, the protein sequence for the gulonolactone (L-) oxidase (GLO) from Rattus norvegicus (accession: gi-92090602-sp-P10867.3-GGLO_RAT) can be back-translated to provide a 1.3 kb DNA sequence that can be used as a template to design 90 polynucleotide variants, each encoding a variant polypeptide having a different combination of from three to five amino acid substitutions. For example, a list of 90 permutations of from 3 to 5 amino acid substitutions can be selected from the following list of 10 possible substitutions: T28S, D95A, S156N, G175S, R212D, I251E, F302S, H330I, Y370G, and K423N. The 90 different permutations of amino acid substitutions encoded by the polynucleotide variants were as follows: D95A/F302S/H330I/K423N; D95A/F302S/Y370G; D95A/G175S/H330I; D95A/G175S/H330I/Y370G/K423N; D95A/G175S/R212D/F302S/Y370G; D95A/G175S/R212D/H330I; D95A/G175S/R212D/Y370G/K423N; D95A/I251E/F302S/K423N; D95A/I251E/H330I; D95A/I251E/K423N; D95A/I251E/Y370G; D95A/R212D/F302S; D95A/R212D/I251E/F302S; D95A/S156N/F302S/H330I/K423N; D95A/5156N/G175S; D95A/S156N/G175S/H330I/Y370G; D95A/S156N/G175S/I251E/F302S; D95A/S156N/I251E/H330I; D95A/S156N/I251E/F302S; D95A/S156N/I251E/K423N; D95A/S156N/K423N; D95A/S156N/R212D/I251E; F302S/H330I/K423N; G175S/F302S/Y370G/K423N; G175S/H330I/K423N; G175S/I251E/F3025; G175S/R212D/H330I; G175S/R212D/I251E/H330I; G175S/R212D/K423N; G175S/R212D/Y370G; G175S/R212D/Y370G/K423N; H330I/Y370G/K423N; I251E/H330I/Y370G; I251E/H330I/Y370G; I251E/Y370G/K423N; R212D/F302S/Y370G/K423N; R212D/H330I/K423N; R212D/I251E/F302S; R212D/I251E/F302S/H330I; R212D/I251E/Y370G; R212D/I251E/Y370G; S156N/F302S/H330I; S156N/F302S/K423N; S156N/F302S/Y370G; S156N/G175S/F302S/Y370G; S156N/G175S/I251E/F302S; S156N/G175S/K423N; S156N/G175S/K423N; S156N/G175S/R212D/F302S/H330I; S156N/I251E/F302S/H330I; S156N/I251E/H330I/Y370G; S156N/I251E/H330I/Y370G/K423N; S156N/I251E/Y370G; S156N/R212D/F302S/H330I/Y370G; S156N/R212D/K423N; T28S/D95A/G175S/F302S; T28S/D95A/G175S/F302S/Y370G; T28S/D95A/H330I; T28S/D95A/I251E; T28S/D95A/I251E/F302S/K423N; T28S/D95A/R212D; T28S/D95A/S156N/H330I/Y370G; T28S/D95A/S156N/R212D; T28S/D95A/S156N/R212D; T28S/D95A/S156N/R212D/Y370G; T28S/D95A/Y370G; T28S/D95A/Y370G/K423N; T28S/F302S/K423N; T28S/G175S/H330I; T28S/G175S/H330I/Y370G; T28S/G175S/I251E/F302S; T28S/G175S/I251E/F302S/Y370G; T28S/G175S/I251E/H330I; T28S/G175S/I251E/K423N; T28S/H330I/K423N; T28S/I251E/F302S/H330I/K423N; T28S/R212D/F302S/H330I; T28S/R212D/H330I; T28S/R212D/I251E/F302S; T28S/R212D/I251E/Y370G/K423N; T28S/R212D/Y370G; T28S/S156N/F302S/H330I/Y370G; T28S/S156N/F302S/Y370G; T28S/S156N/F302S/Y370G; T28S/S156N/G175S; T28S/S156N/G175S; T28S/S156N/G175S/I251E; T28S/S156N/G175S/I251E/K423N; T28S/S156N/R212D/I251E/H330I; T28S/S156N/R212D/I251E/K423N; and T28S/S156N/R212D/K423N.

Software (e.g., as described in FIGS. 4-6) can be used to determine a total of only 55 amplicons, corresponding to polynucleotide variant fragments with overlapping regions of sequence, can be used to assemble the 90 polynucleotide variants in a Round 2 SOE-PCR reaction. Software also can be used to determine that a total of only 22 oligonucleotide primers are needed in 55 separate Round 1 PCR reactions with the 1.3 kb reference polynucleotide as template to generate the necessary 55 amplicons. The 22 oligonucleotide primers are only 30 or 33 nucleotides in length, and include mutagenic primers comprising nucleotide changes in the middle of the sequence (e.g., at nucleotides 15-17).

Thus, in accordance with the methods disclosed herein, construction of the 90 different polynucleotide variants requires synthesis of only 22 relatively short oligonucleotides (30-mer to 33-mers), a first Round 1 PCR reaction to create the 55 amplicons (i.e., polynucleotide variant fragments), and a second Round 2 SOE-PCR reaction in which the 55 amplicons are pooled in various combinations (with forward and reverse flanking primers) to allow SOE-PCR assembly of the 90 polynucleotide variants. In preparing the Round 2 SOE-PCR reactions, each of the 55 amplicons can be reused on average 7.8 times, with certain fragments used only once or twice, and others used as many as 36 times.

The workflow of the Round 1 and Round 2 reactions can be controlled by software-generated worklists (e.g., as in FIGS. 4 and 6) which are used to run the Tecan robotics for the liquid handling The worklists for this illustrative 90 variant library construction call for only 110 liquid handling operations for the Round 1 PCR reactions to generate the 55 amplicons using 22 primers, and only 430 liquid handling operations for the Round 2 SOE-PCR assembly reactions to prepare the 90 full length polynucleotide variants from the 55 amplicons.

The accuracy of the polynucleotide variant sequences provided by the methods disclosed herein can be determined by further steps of cloning and sequencing each of the plurality of constructs from the Round 2 reactions. As illustrated by the Examples (below), the methods disclosed herein result in surprisingly high level of correct sequences (full-length perfect (FLP) sequences)—i.e., sequences which have the desired nucleotide changes relative to the reference polynucleotide.

At least some of the surprising advantages of the methods disclosed herein are in the greater accuracy of the large polynucleotide variant libraries produced. In some embodiments, the methods can be used to prepare an addressable library of at least 10 different polynucleotide variants, each comprising at least one defined sequence difference relative to a reference polynucleotide sequence, wherein at least an average of 75% of the polynucleotide variant sequences are correct sequences (e.g., the sequences comprising the full length reference sequence with the defined nucleotide differences introduced by the primers used in the method). In some embodiments, the methods provide an addressable library of at least 10, 20, 30, 40, 50, 60, 70, 80, 90, 100, 150, 200 or more different polynucleotide variants, each comprising at least one defined sequence difference relative to a reference polynucleotide sequence, wherein at least 75%, 80%, 85%, 90%, 95% or greater of the polynucleotide variant sequences are correct—e.g., FLP by sequence analysis.

In certain embodiments, the methods disclosed herein comprising a plurality of Round 1 PCR reactions using a reference polynucleotide template and a plurality of Round 2 SOE-PCR amplicon assembly reactions can be used to prepare an addressable library of 10 or more polynucleotide variants of reference polynucleotide of at least 500 bp, 750 bp, 1000 bp, 1250 bp, 1500 bp or more, each variant comprising from about 1-30, 1-25, 1-20, 1-15, 3-30, 3-20, or 3-15 nucleotide changes relative to the reference polynucleotide, wherein the Round 1 PCR reactions comprise about 6-300, 6-200, 6-100, 6-50, 6-40, 6-30, 6-25, 6-20, 6-15, or as few as 6-10 different oligonucleotide primers, and at least 75%, 80%, 85%, 90%, 95% or greater of the polynucleotide variant sequences are full-length perfect.

In some embodiments, various permutations of polynucleotide fragments (e.g., selected from an addressable library) can be assembled into an addressable library of polynucleotide variants each encoding a different variant polypeptide having a defined amino acid residue difference. Each of these polynucleotide variants can then be cloned into an expression system to generate an addressable library of clones, each capable of generating a different variant polypeptide. This addressable library of clones can be transformed into cells (e.g., E. coli), for translation, and automated plating and picking of colonies (i.e., viable transformants). Sequencing then can be carried out to confirm the combination of mutations in each variant polypeptide sequence so generated. Assay (e.g., via high-throughput screening) of the variant polypeptides for desired altered traits can be carried out on all of the variant polypeptides, or optionally on only those variant polypeptides confirmed by sequencing as having the desired combination of mutations.

Although in some embodiments the present disclosure provides methods resulting in an addressable library of polynucleotide variants having defined differences at targeted positions, in some embodiments of the methods it is preferable to combine (or pool) the polynucleotide variants. Pooling of the very well-defined and diverse libraries of polynucleotide variants provided by the methods described herein results in the counterintuitive and surprising advantage of allowing more efficient transformation and screening of a broader range polynucleotide sequence diversity and identification of variants of interest (e.g., "hits" having improved properties), prior to carrying-out resource-intensive and time-consuming sequencing. Thus, this method allows the researcher to create and screen a large, well-defined sequence diversity space of the polynucleotide variant library, and focus on sequencing only variants of interest. The pooling before transformation advantage allows efficient screening of extremely large diversity libraries, for example a survey of a library of polynucleotide variants encoding polypeptides having a complete set of 20 amino acid residue differences at every position, and only that single defined difference in every member of the library.

The unexpected advantage of pooling an addressable library of variants prior to transformation is believed to arise in part from the capability of the method of synthesizing polynucleotide variants disclosed herein for producing the desired variants with an average of 85% or greater accuracy (i.e., percentage production of the full-length polynucleotide variants having the defined difference(s) at the targeted positions). Other methods for generating libraries of diverse polynucleotides, such as error-prone PCR, result in a relatively broad distribution of mutations (e.g., 37% with no mutation, 37% with desired one mutation, and 26% with two or more mutations). Furthermore, the methods of the present disclosure are capable of accessing all 19 amino acid substitutions at every position of an encoded polypeptide. A comparative analysis of random mutagenesis using error-prone PCR shows that it only accesses about 45% of these mutations that are accessed by the methods of the present disclosure. Due to this much greater accuracy, and accessibility to diversity (accurate single and multi-site variants), pooled libraries of polynucleotide variants made by the methods of the present disclosure can be screened more efficiently. For example, single-position variants comprising all 20 amino acids at each of 20 positions of a 1.2 kb reference polynucleotide encoding a polypeptide were synthesized and pooled, and the resulting pool of variants cloned, transformed, and plated on 19 plates (88 data wells/plate). Screening of those 19 plates yields polynucleotide variants encoding 361 unique polypeptides having a single amino acid difference from the reference polypeptide. This result represents 95% screening coverage of the pooled library in only 19 plates.

Accordingly, in some embodiments of the methods of the present disclosure, the resulting plurality of polynucleotide variants having at least one defined difference relative to a reference polynucleotide are combined. In some embodiments, the pooled variants are then cloned into an expression system, thereby creating a pooled library of clones. This pooled library of clones can be transformed (e.g., in a single transformation step) into cells for translation, plating, and picking of colonies (i.e., viable transformants). Assay of colonies from this pooled library of clones can be carried out (e.g., via high-throughput screening) before sequencing to identify polynucleotide variants encoding polypeptides having desired altered traits. Once such "hit" for an altered trait is identified, it can be sequenced to determine the specific combination of mutations present in the polynucleotide variant sequence. Optionally, those variants encoding polypeptides not having the desired altered traits sought in assay need not be sequenced. Accordingly, the pooled library of clones method can provide more efficiency by requiring only a single transformation rather than a set of parallel transformation reactions.

In an alternative embodiment, the method can be carried out wherein an addressable library of polynucleotide variants having at least one defined difference relative to a reference polynucleotide are separately cloned into an expression system—e.g., using a megaprimer reaction (see e.g., Tyagi et al., BMC Biotechnology 2004, 4:2; doi:10.1186/1472-6750-4-2). This addressable library of clones (e.g., expression vectors each comprising a polynucleotide variant of the addressable library) can then be pooled and transformed in a single step into cells for translation, plating, and picking of colonies, and screening as described above.

Analogously, the method can also be used to generate various permutations of mutation combinations to examine the structural features of biologically important proteins. For example, receptors involved in signal transduction of extracellular molecules act via interaction with other receptors as well as various intracellular proteins. These complex interactions can affect different cellular signaling processes from the same type of receptor molecule. Both negative and positive signaling can be initiated by the same receptor. A specific example is G-coupled protein receptors, which interact with βγ, Gsα, and Giα proteins. See, e.g., Morris et al., 1999, Physiol. Rev. 79:1373-1430. Because mutations at different domains of the receptor can have different effects, the methods herein provide an efficient process for generating different permutations of mutation combinations known to affect different aspects of receptor function, thereby permitting studies on the structural and associated biological functions of the protein of interest.

While the methods for generating different permutations of a polynucleotide sequence have been illustrated for generating polynucleotides encoding various permutations of a polypeptide from a defined set of amino acid residue differences, it is to be understood that the methods can be adapted generally for generating permutations of polynucleotide sequences. For example, the methods herein can be used to generate different permutations of functional polynucleotides, such as genes for ribosomal RNAs. Various rRNAs form nucleoprotein complexes that participate in protein synthesis in prokaryotes and eukaryotes. Many antibiotics function by disrupting ribosome function and are known to interact with defined regions of certain rRNAs. Various mutations have been identified that affect protein synthesis and these regions are correlated with sites of interaction with antibiotics. See, e.g., Yassin et al., 2005, Proc Natl Acad. Sci. USA 102(46):16620-16625.

Using the methods described herein, various permutations of known mutations affecting ribosomal RNA function can be synthesized and the effects of certain combination of mutation examined Other applications will be apparent to the skilled artisan.

6. EXAMPLES

Example 1

Preparation of Amplicons

Oligonucleotide Preparation. Oligonucleotide primers at 200 uM concentration are diluted to 4 uM with sterile water in an Axygen HalfDeep 96 (1.1 mL) plate. For most positions on the microtiter plate, adding 10 μL of oligonucleotide to 490 μL $dH_2O$ will be sufficient. For positions A01 and D01 on the oligonucleotide plate, the common forward and reverse primers, a larger volume may be required. The maximum aspiration volumes in the output report in the aspirate and dispense volumes section is verified prior to the next step. Primers may be pooled in equimolar or non-equimolar ratios after dilution and prior to use for amplicon formation (see e.g., Examples 6-8).

Round 1—Formation of Amplicons by PCR. Tecan robotics are used to aliquot 5 μL of each forward and reverse oligonucleotide primer into BioRad HardShellPCR96 plates (Tecan script output) and to add 40 μL of master mix. Perform Round 1 PCR and verify amplification using a 2% 96 well e-gel. Reagent for the PCR is as follows: 5 μL 10× Herculase buffer, 1 μL 40 mM dNTPs, 1 μL of 100 ng/μL of SOE template, 2.5 units Herculase polymerase (Stratagene, La Jolla, Calif., USA). PCR is carried out as follows: 2 min denaturation at 95° C. followed by cycling at 95° C. for 30 s, 56° C. for 30 s, 72° C. for 1 min/Kb. The number of cycles is 17.

Treatment with ExoSAP-it. For Round 1 of PCR, 25 μL of the reaction product is transferred to a fresh 96 well plate, and 2 μL ExoSAP-It (USB Corp., Ohio, USA) plus 0.5 μL DpnI is added and cycling performed (manual transfer 37° C. 1 hour 80° C. 15 min) Samples are diluted to a final volume of 100 μL by the addition of 73 μL $dH_2O$ and pooled into another BioRad HardShellPCR96PCR plate using a Tecan script.

Example 2

Assembly of Amplicons and Analysis of Products

Round 2—Assembly and SOE-PCR. Tecan robotics are used to aliquot a 15 μL pool of fragments (i.e., Round 1 amplicons) into BioRad HardShellPCR96 plates (Tecan script output) and to add 35 μL of master mix (5 μL of 10× Herculase Buffer, 1 μL of 40 mM dNTPs, 0.2 μL of forward primers, 0.2 μL of reverse primers, 2.5 units Herculase enzyme, and 28.1 μL $dH_2O$). Amplicons can be pooled in equimolar or non-equimolar amounts (see e.g., Examples 6-8). PCR is performed and amplification verified using a 2% 96 well E-gel. PCR is carried out as follows: 2 min denaturation at 95° C. following by cycling at 95° C. for 30 s, 56° C. for 30 s, 72° C. for 1 min/Kb. The number of cycles is 17.

96-well plate purification. Purify all samples using Zymo ZR-96 PCR clean up 96 well plates (manufacturers protocol with the following modifications) (Zymo Research, Calif., USA). Perform all centrifuge steps at 2800 rpm for 10 minutes. To elute the DNA, apply 25 μL $dH_2O$ of temperature 55° C. directly to the silica membrane, spin for 10 minutes and repeat. Using this method 48-50 μL of product is recovered. At this point products can be pooled in desired combinations prior to digestion and cloning.

Restriction enzyme BglI digestion. BgI digestion is for cloning into BglI site of an expression vector. Transfer 30 μL of each purified product or pool of products into a fresh semi-skirted PCR plate, add 20 μL of BglI digestion master mix (5 μL 10×NEB Buffer 3, 13 μL $dH_2O$, 20 units BglI (New England Biolabs, Mass., USA)) to all samples and incubate at 37° C. for 4 hrs.

96-well plate purification. Purify all samples using Zymo ZR-96 PCR clean up 96-well plates according to manufacturer's protocol with the following modifications: (1) perform all centrifuge steps at 2800 rpm for 10 minutes; (2) to elute DNA, apply 25 μL $dH_2O$ at 55° C. directly to the silica membrane, spin for 10 min, and repeat. Using this method, 48-50 μL of product is recovered. Verify product recovery using a 2% 96 well E-gel.

Ligations to expression vector. Transfer 3 μL of each purified insert to a fresh plate and add 27 μL of ligation master mix (3 μL 10× Ligase Buffer (New England Biolabs, Mass., USA), 1 μL BglI digested vector (50 ng/μL), 400 units T4 Ligase (New England Biolabs, Mass., USA), 22 μL dH$_2$O) to the samples. Incubate for 14 hours at 16° C. followed by 15 minutes at 65° C., followed by 8° C. hold.

HTP-Transformation. Transfer 2 μL of each ligation reaction to 20 μL of TSS chemically competent cells and incubate on ice in a metal block for at least 15 min. Heat shock at 42° C. for 35 seconds and return to the metal block for 2 min. Add 80 μL of 37° C. SOC media to each sample. Incubate at 37° C. for 1 hour before plating.

Plating. Use Tecan to plate 40 μL per well of transformation mixture onto 48-well divided Q-trays. Dispense three 5 mm bead to each well using a bead dispenser. Grow the transformants overnight at 37° C.

Picking and culturing. For assay and/or sequence analysis master plates are generated by picking individual colonies from the Q-trays to inoculate the wells of Nunc flat bottom plates containing LB, CAM, and 1% glucose. For sequence verified plates, two colonies per Q-tray well are picked into two separate Nunc flat bottom plates. For non-sequence verified variant plates, three colonies per Q-tray are picked into three separate Nunc flat bottom plates.

Colony PCR Colony PCR is carried out on at least one master plate by adding 2 μL of that culture to the standard colony PCR master mix and performing PCR. ExoSAP-it is used to clean up the PCR product as follows: (1) transfer 5 μL of PCR sample to a new PCR plate containing 2 μL ExoSAP-it; (2) incubate at 37° C. for 15 min and 80° C. for 15 min; and (3) dilute the samples to a final volume of 40 μL by adding 33 μL of dH$_2$O.

Sequencing of PCR products. Add 4 μL of 1 mM sequencing primer to the sequencing plate. Add 4 μL of cleaned up PCR sample to create template/primer mix which are then used for standard cycle sequencing.

Example 3

Generation of a Set of 190 Different Polynucleotide Variants Each Encoding a Polypeptide Having a Single Amino Acid Change Relative to a Reference Polypeptide Experimental design: A reference polynucleotide of 1359 bp (encoding an enzyme of 453 amino acids) was selected. A total of 190 amino acid residue differences from the reference sequence were selected based upon sequence changes seen in homologous enzymes. The 190 variants were made as individual polynucleotides encoding the 190 different proteins to be expressed and tested. Each of the 190 polynucleotide variants was assembled by combining two amplicons comprising the desired single codon change in their overlap region (as prepared in Round 1 below) in a SOE reaction (Round 2 below).

Oligonucleotide preparation: A total of 382 oligonucleotide primers for PCR were designed and synthesized according to standard methods. Oligonucleotides were generally 31 nucleotides (nt) in length with the desired change(s) to the codon of interest located in the middle (~base 15) of the oligonucleotide primer. All oligonucleotides were diluted to 4 μM with sterile water in an Axygen HalfDeep 96 (1.1 mL) plate.

Round 1—Formation of Amplicons by PCR: Each amplicon, corresponding to a polynucleotide variant fragment, was generated in a PCR reaction using a vector comprising 1359 nt reference polynucleotide as template and using a mutagenic primer in combination with a common flanking primer (annealing to the vector upstream or downstream of the gene containing no mutation). Reaction workflow, conditions and clean-up were as described in Example 1.

Figure 3:
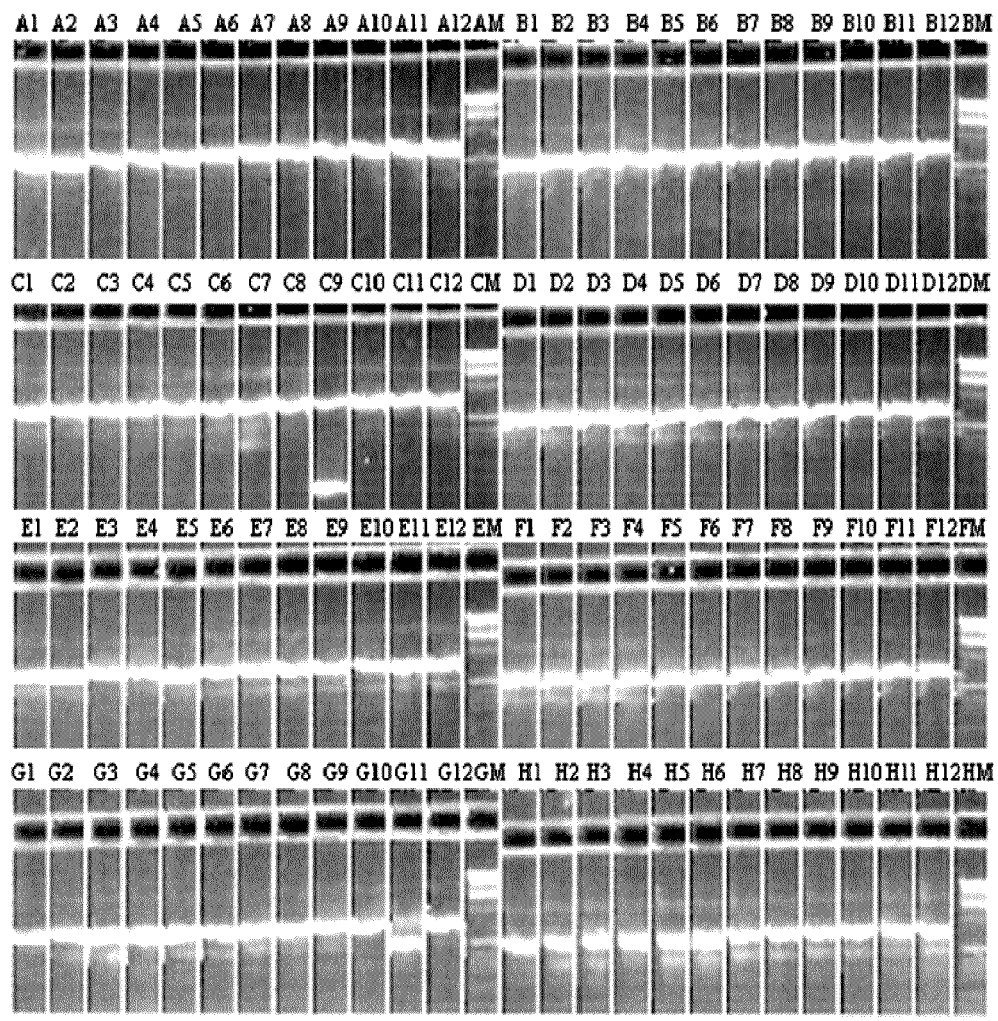
FIG. 3 shows the agarose gels of 96 samples (and 8 controls) resulting from assembling the overlapping polynucleotide fragments and replicating the assembled polynucleotide fragments to synthesize the polynucleotide variants encoding the desired polypeptide variant. Nearly every gel showed a single strong band indicating the expected length sequence was present.

Round 2—Assembly of Amplicons. Purified amplicons from Round 1 were pooled such that 2 amplicons with overlapping regions comprising the desired codon sequence change for each of the 190 polynucleotide variants and each pool was aliquoted into the well of a 96-well plate as described in Examples 1 and 2. Common flanking forward and reverse primers were added to each pool and PCR was carried out as described in Example 2 resulting in assembly of the amplicons (i.e., polynucleotide fragments) to form the full length polynucleotide variant. The assembly reactions were inspected by agarose gel and found to contain product of the expected size. (See e.g., FIG. 3.)

Sequence Analysis of Polynucleotide Variants. After purification using Zymo ZR-96 PCR clean up, products were cloned into an expression vector, and each ligation was transformed into E. coli host cells. Two colonies from each transformation were picked and plasmid DNA was prepared for DNA sequencing. One sample from each transformation was sequenced using sequencing primers internal to and flanking the gene. Of the 190 polynucleotide variants, 160 (84%) were shown to have only the full length perfect (FLP) sequence with the desired codon sequence changes. By sequencing the second plasmid preparation of the 30 variants that were incorrect, 25 additional correct sequences were identified. This brought the overall success rate to 97% correct sequences. (185 of the desired 190 polynucleotides were identified.) The polynucleotides were expressed and the variant polypeptides assayed.

Example 4

Generation of a Set of 96 Different Polynucleotide Variants Each Encoding a Polypeptide Having a Three Amino Acid Changes Relative to a Reference Polypeptide Experimental Design: A reference polynucleotide of 1359 nt was selected. 96 variants were designed, each containing three mutations relative to the reference sequence. The 96 variants were made as individual polynucleotides each encoding one of 96 different proteins to be expressed and tested. Each of the 96 polynucleotide variants was assembled by combining four amplicons comprising the desired codon changes in their overlap region (as prepared in Round 1 below) in a SOE reaction (Round 2 below).

Oligonucleotide Preparation: A total of 130 oligonucleotide primers were designed and synthesized according to standard methods. Oligonucleotides were generally 31 nt in length with the desired change(s) to the codon of interest in the middle (~base 15) of the oligonucleotide. All oligonucleotides were diluted to 4 μM with sterile water in an Axygen HalfDeep 96 (1.1 ml) plate.

Round 1—Formation of Amplicons by PCR: Each amplicon, corresponding to a polynucleotide variant fragment, was generated in a PCR reaction using a vector comprising 1359 nt reference polynucleotide as template and using a mutagenic primer in combination with another mutagenic primer or a common flanking primer (annealing to the vector upstream or downstream of the gene containing no mutation). Reaction workflow, conditions and clean-up were as described in Example 1.

Round 2—Assembly of Amplicons. Purified amplicons from Round 1 were pooled such that 4 amplicons with overlapping regions comprising the desired codon sequence changes for each of the 96 polynucleotide variants and each pool was aliquoted into the well of a 96-well plate as described in Examples 1 and 2. Common flanking forward and reverse primers were added to each pool and PCR was carried out as described in Example 2 resulting in assembly of the amplicons (i.e., polynucleotide fragments) to form the full length polynucleotide variant. The assembly reactions were inspected on an agarose gel and found to contain product of the expected size. (See e.g., FIG. 3.)

Sequence analysis of Polynucleotide product. After purification using Zymo ZR-96 PCR clean up, products were cloned into an expression vector, and each ligation was transformed into E. coli host cells. Two colonies from each transformation were picked and plasmid DNA was prepared for DNA sequencing. One sample from each transformation was sequenced using sequencing primers internal to and flanking the gene. Of the 96 polynucleotide variants, 82 (85%) were determined to have only the correct FLP sequence with the desired changes.

Example 5

Generation of a Set of 96 Different Polynucleotide Variants Each Encoding a Polypeptide Having from One to Six Amino Acid Changes Relative to a Reference Polypeptide Experimental design: A reference polynucleotide of 1056 nt was selected. 96 variants were designed, each containing from one (1) to six (6) mutations from the reference sequence. The 96 variants were made as individual polynucleotides each encoding one of the 96 different proteins to be expressed and tested. Each of the 96 polynucleotide variants was assembled by combining from two (e.g., for variant encoding a single amino acid change) to seven (e.g., for variant encoding six amino acid changes) amplicons comprising the desired codon changes in their overlap region (as prepared in Round 1 below) in a SOE reaction (Round 2 below).

Oligonucleotide preparation: A total of 108 oligonucleotide primers were designed and synthesized according to standard methods. Oligonucleotides were generally 31 nt in length with the desired change(s) to the codon of interest in the middle (~base 15) of the oligonucleotide. If two amino acid changes were close together, a longer oligonucleotide was designed to encode for both changes to be incorporated. All oligonucleotides were diluted to 4 μM with sterile water in an Axygen HalfDeep 96 (1.1 mL) plate.

Round 1—Formation of Amplicons by PCR: Each amplicon, corresponding to a polynucleotide variant fragment, was generated in a PCR reaction using a vector comprising 1056 nt reference polynucleotide as template and using a mutagenic primer in combination with another mutagenic primer or a common flanking primer (annealing to the vector upstream or downstream of the gene containing no mutation). Reaction workflow, conditions and clean-up were as described in Example 1.

Round 2—Assembly of Amplicons. Purified pooled amplicons (from 2 to 7 amplicons/polynucleotide) were aliquoted into plates as described in Example 1. Common flanking forward and reverse primers were added and PCR was carried out as described in Example 1.

Sequence Analysis of Polynucleotide Product. After purification using Zymo ZR-96 PCR clean up, products were cloned into an expression vector, and each ligation was transformed into E. coli host cells. Two colonies from each transformation were picked and plasmid DNA was prepared for DNA sequencing. One sample from each transformation was sequenced using sequencing primers internal to and flanking the gene. As shown in Table 1 (below), of the 96 polynucleotide variants, 72 (75%) were shown to have only the correct FLP sequence with the desired 2-7 codon changes.

TABLE 1

| 96 Variants Constructed - 88 Variants Required to Make Final Plate | | | |
|---|---|---|---|
| Sequencing Set | 1 (n = 96) | 2 (n = 96) | 3 (n = 16) |
| Total Correct | 72 | 84 | 92 |
| Failed Sequences | 5 | 3 | 2 |
| Cross Contamination | 5 | 2 | 0 |
| Coding Mutations | 8 | 2 | 0 |
| Indels | 6 | 4 | 2 |

Example 6

Generation of a Pooled Set of 82 Specific Polynucleotide Variants, Each Encoding for a Polypeptide Containing a One Amino Acid Mutation from a Reference Polynucleotide Experimental design: A total of 82 specific residues in an enzyme having 413 amino acids were targeted for mutation. The wild-type enzyme is encoded by a reference polynucleotide sequence of 1242 bp. 82 specific polynucleotide variants each containing one of the 82 mutations are prepared separately by designing and synthesizing primers, generating amplicons, and assembling pairs of amplicons to synthesize a set of full-length polynucleotide variants comprising each of the mutations. All of the full length polynucleotide variants are then pooled together prior to purification, cloning and transformation. Pooling prior to transformation reduces workload (as compared to doing all cloning and transformation steps separately for each gene variant). After colony picking and expression, the enzyme variants are screened and interesting gene variants are sequenced to identify the mutation of interest.

Oligonucleotide primer preparation: For each of the 82 desired mutations, two mutagenic oligonucleotide primers (one forward and one reverse) were designed that included the desired polynucleotide codon sequence change relative to the reference sequence. The primers were 33 nucleotides in length with the targeted position was located in the middle of the oligonucleotide. All oligonucleotides were synthesized according to standard methods and diluted to 4 μM with sterile water in an Axygen HalfDeep 96 (1.1 mL) plate.

Round 1—Formation of Amplicons by PCR: For each of the 82 positions, two amplicons were generated with overlapping regions comprising the desired codon change at that position. Each amplicon was generated in a PCR reaction using a vector containing the 1242 nt reference polynucleotide as template and a mutagenic primer in combination with a common flanking primer (annealing to the vector upstream or downstream of the gene). Reaction workflow, conditions and clean-up were as described in Example 1.

Round 2—Assembly of Amplicons. For each of the 82 polynucleotide variants, the two purified amplicons with overlapping regions comprising the desired codon change (from Round 1 reaction) were combined. Common flanking forward and reverse primers were added to each of 82 wells and SOE-PCR was carried out as described in Example 2 resulting in assembly of the amplicons (i.e., polynucleotide fragments) to form the 82 full-length polynucleotide variants. Inspection of the assembly reactions was carried out on an agarose gel and all 82 reactions were found to contain product of the expected size. These full length products for all 82 reactions were pooled together.

Pooled Cloning and Transformation of the Full-Length Polynucleotide Variants. The pooled products from the assembly reactions were purified using a Qiagen kit, digested with restriction enzyme, cloned into an expression vector, transformed into host cells, and plated onto solid LB media containing glucose and chloramphenicol.

Further screening of the polypeptides encoded by the polynucleotides to identify "hits" (e.g., polypeptides exhibiting some improved property or activity over the wild-type) is carried out using the transformants in standard high-throughput assays.

Sequence Analysis of Polynucleotide Variants. Eight variants were selected at random for sequencing. Each variant was found to contain one desired mutation. No random mutations were observed.

Example 7

Generation of a Pooled Set of Polynucleotide Variants Encoding 912 Polypeptides, Each Having a Single Amino Acid Change Relative to a Reference Polypeptide Experimental design: A reference polynucleotide of 1383 bp (encoding an enzyme of 460 amino acids) was selected. Amino acid residues at 48 different positions of the enzyme were selected for complete saturation mutagenesis (i.e., generation of all 19 amino acid residue changes at each of the 48 positions). A reduced set of 23 codons, comprising TGG and the NNT and VWG reduced codon sets, which is capable of encoding all possible amino acid changes is used. For each position, all 23 possible polynucleotides comprising the 23 different codons at that position were assembled simultaneously by combining in a SOE-PCR reaction (Round 2 reaction below) two sets of amplicons (prepared in Round 1 reaction), where each of the sets of amplicons comprise the 23 different codons at the targeted position in their overlap region. The resulting plurality of polynucleotide variants that are constructed include all 23 different codons at each of the 48 different positions. These variants are then combined into one pool before ligating and transforming to generate clones. Sequencing is then carried out on random clones to confirm that the full-length variant genes were prepared and/or on "hits" identified by subsequent screening assays carried out on the clones.

Oligonucleotide primer preparation: For each selected amino acid position, 6 oligonucleotide primers were designed. The oligonucleotides were 33 nucleotides in length with the codon to be altered located in the middle of the sequence (e.g., at position 17). Three oligonucleotides were designed in the 'forward' direction, while the other three were complements in the 'reverse' direction. Four of the oligonucleotides were degenerate and two were specific. Two of the primers were specific oligonucleotides including the "TGG" codon (or the reverse complement "CCA") encoding tryptophan at the center. The other 4 primers were sets of degenerate oligonucleotides including either a codon from either of the reduced codon sets "VWG" or "NNT" (or their reverse complements "CWB" or "ANN") at their centers and otherwise were identical to the reference polynucleotide at all other positions.

All oligonucleotide primers were synthesized according to standard methods and diluted to 4 µM with sterile water in an Axygen HalfDeep 96 (1.1 mL) plate. The three 'forward' primers (containing the "NNT", "VWG" and "TGG" codons) were combined at a molar ratio of 16:6:1, respectively. The 'reverse' oligonucleotides containing the "ANN", "CWB" and "CCA" codons were similarly pooled.

Round 1—Formation of Amplicons by PCR: Two amplicon pools (i.e., sets of PCR products comprising all 23 codons) were generated for each of the 48 positions that were targeted for saturation mutagenesis. Each pool of amplicons was generated in a PCR reaction using a vector containing the 1383 nt reference polynucleotide as template and the pooled mutagenic primers (described above) in combination with a common flanking primer (annealing to the vector upstream or downstream of the gene). Otherwise reaction workflow, conditions, and amplicon clean-up and purification were as described in Example 1.

Round 2—Assembly of Amplicons. The purified amplicon pools from Round 1 were combined such that the pairs of amplicons with overlapping regions comprising the 23 desired codon changes for each of the 48 positions were aliquoted into wells of a 96-well plate as described in Examples 1 and 2. Common flanking forward and reverse primers were added to each well and SOE-PCR was carried out as described in Example 2 resulting in assembly of the overlapping amplicons (i.e., polynucleotide fragments) to form pools of full-length polynucleotide variants (i.e., sets of polynucleotides having 23 different codons at one of the 48 positions). Inspection of these SOE-PCR assembly reactions were carried out on an agarose gel and found to contain full-length products of the expected size.

Pooled Cloning and Transformation of the Full-Length Polynucleotide Variants. The 48 pools of full-length polynucleotide variants from the 48 assembly reactions then were pooled together. This final pool should include full-length polynucleotides each having at only one of the 48 targeted positions, one of the 23 codons from the reduced codon set. Thus, a total of 1056 (22 codon changes×48 positions) different polynucleotide variants encoding 912 different polypeptides (19 amino acid changes×48 positions) should be present.

The pooled full-length polynucleotides were purified using a Qiagen kit and then cloned into an expression vector, transformed into host cells, and plated onto solid LB media containing glucose and chloramphenicol.

Further screening of the polypeptides encoded by the polynucleotides to identify "hits" (e.g., polypeptides exhibiting some improved property or activity over the wild-type) is carried out using the transformants in standard high-throughput assays.

Sequence Analysis of Polynucleotide Variants. Twenty-four colonies were selected at random for sequence analysis. Plasmid prepared from each transformant was sequenced using sequencing primers internal to and flanking the gene. Of the 24 polynucleotide variants, 19 (80%) were found to have the desired result of a full-length gene containing one amino acid change at a targeted position and no additional mutations. Two genes appeared to have two amino acid changes that were attributed to contaminated transformations (double transformants.) One gene was found to have two amino acid changes, one of which arose from a random mutation at a non-targeted position. Two were found to have no amino acid changes but did contain a silent mutation. These silent variants are to be expected when using degenerate codon sets.

Example 8

Generation of a Pooled Set of Polynucleotide Variants Comprising Stochastic Mixes Defined Mutations Encoding from 0 to 13 Amino Acid Residue Differences in a Reference Polypeptide Experimental design: A reference polynucleotide of 1632 bp (encoding an enzyme of 543 amino acids) was selected. Thirteen (13) defined amino acid changes in the reference sequence were selected for preparation alone and in various combinations. By mixing mutagenic primers coding for the defined mutations with non-mutagenic primers, a mixture of amplicons is prepared comprising the 13 defined mutations alone or in combination, or no mutations at all. All amplicons are then combined into a single assembly reaction to generate a pool of full-length polynucleotide variants (encoding genes) that contains stochastic mixes of the defined mutations. This mixture of full length genes (the gene library) is then ligated into the expression vector and transformed to the host organism.

Oligonucleotide primer preparation: For 11 of the defined mutations, a pair of mutagenic primers (one forward and one reverse) were designed that include the nucleotide difference(s) encoding the desired amino acid change. In addition, two non-mutagenic primers were designed for each mutated position. The oligonucleotides primers were 33 nucleotides in length and the position of the nucleotide differences (e.g., changed codon) was located in the middle of the oligonucleotide. Two of the defined amino acid residue differences in the reference polypeptide were located very close to each other at amino acid positions 173 and 176. For these two positions, four forward and four reverse primers were designed as follows: one primer having neither of the two mutations; two primers each having one of the two mutations; and one primer having both of the mutations. All primers were synthesized according to standard methods and diluted to 4 μM with sterile water in an Axygen HalfDeep 96 (1.1 mL) plate. The two forward and two reverse primers (one containing the mutation, and one non-mutagenic) for each position, or the four forward and four reverse primers (in the case of positions 173/176) were combined at a molar ratio of 1:2 (mutagenic: non-mutagenic).

Round 1—Formation of Amplicons by PCR: A total of 13 amplicon mixtures was generated in a PCR reaction mix containing a vector containing the 1632 nt reference polynucleotide as template and the 1:2 molar ratio of mutagenic to non mutagenic primers for the position(s) of interest. The 5'-end and 3'-end amplicons were prepared using mixed primers for one end and a common flanking primer (annealing to vector upstream or downstream) for the other. All other amplicons used mixed primers for both ends. Most amplicons therefore contained no mutation, one mutation (e.g., at 5'-end or 3'-end), or two mutations. Reaction workflow, conditions and clean-up were as described in Example 1.

Round 2—Assembly of Amplicons. The 13 mixtures of purified amplicon from Round 1 were pooled and common flanking forward and reverse primers added. SOE-PCR was carried out as described in Example 2 resulting in assembly of the amplicons (i.e., polynucleotide fragments) into a pooled sample of full length polynucleotide variants. Analysis of the assembly reaction on an agarose gel indicated that it contained full-length products of the expected size.

Pooled Cloning and Transformation of the Full-length Polynucleotide Variants. The pooled assembly reaction was purified using a Qiagen kit, cloned into an expression vector, transformed into host cells, and plated onto solid LB media containing glucose and chloramphenicol.

Further screening of the polypeptides encoded by the polynucleotides to identify "hits" (e.g., polypeptides exhibiting some improved property or activity over the wild-type) is carried out using the transformants in standard high-throughput assays.

Sequence Analysis of Polynucleotide Variants. A random selection of 31 clones were sequenced and found to comprise the following distribution of full length polynucleotide variants having one or more of the defined mutation (or wild-type): 2 with no mutations; 4 with 1 of the mutations; 8 with 2 of the mutations; 8 with 3 of the mutations; 5 with 4 of the mutations; 3 with 5 of the mutations; 1 with 8 of the mutations. All of the 13 desired mutations were observed in at least one of the sequenced gene variants. All of the variants containing multiple desired mutations had different combinations of mutations.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of synthesizing a plurality of polynucleotide variants each having at least one defined nucleotide difference relative to a single starting reference polynucleotide sequence, the method comprising:
   (a) separately amplifying a single starting reference polynucleotide template with each of a plurality of pairs of forward and reverse mutagenic primers, wherein the plurality of pairs of forward and reverse mutagenic primers comprises the plurality of defined nucleotide differences and wherein each pair generates an amplicon comprising a sequence capable of binding to an adjacent overlapping sequence of at least one other amplicon, wherein the plurality of pairs of forward and reverse primers comprise at least one degenerate primer, and wherein said amplifying is conducted in one round of simultaneous amplification utilizing said plurality of pairs of forward and reverse mutagenic primers to generate said amplicons;
   (b) purifying said amplicons to provide purified amplicons;
   (c) separately assembling a plurality of sets of said purified amplicons, wherein each set comprises amplicons having adjacent overlapping sequences capable of binding to form the full length of the reference polynucleotide sequence, wherein the sequence comprises mutations introduced by said mutagenic primers;
   (d) replicating the plurality of sets of assembled amplicons, thereby synthesizing a plurality of polynucleotide variants; and
   (e) combining the plurality of polynucleotide variants.

2. The method of claim 1, wherein each of the plurality of pairs of forward and reverse primers comprises at least one of the defined nucleotide differences.

3. The method of claim 1, wherein the single starting reference polynucleotide encodes a reference polypeptide and each of the plurality of polynucleotide variants encodes a polypeptide having at least one amino acid sequence difference.

4. The method of claim 1, wherein the method further comprises the step of separately cloning the plurality of polynucleotide variants into expression vectors before they are combined.

5. The method of claim 1, wherein the method further comprises the step of cloning the combined plurality of polynucleotide variants into an expression vector, thereby generating a combined plurality of expression vectors each comprising a polynucleotide variant.

6. The method of claim 5, wherein the method further comprises transforming cells with the combined plurality of expression vectors.

7. The method of claim 6, wherein the method further comprises screening the transformed cells for activity of the polypeptides encoded by the polynucleotide variants.

8. The method of claim 7, wherein the method further comprises isolating at least one polypeptide encoded by the polynucleotide variants.

9. The method of claim 1, wherein the degenerate primer comprises at least one degenerate codon at a position of a nucleotide difference selected from the group consisting of NHT, NNB, NNG, NNK, NNN, NNS, NNT, NDT, RMG, RNG, RRS, SNT, VNS, VNT, and VWG.

10. The method of claim 1, wherein the degenerate primer comprises at a position of a nucleotide difference the codons encoding 20 different amino acids.

11. The method of claim 10, wherein the codons encoding the 20 different amino acids consist of NNT, VWG, and TGG.

12. The method of claim 1, wherein the plurality of polynucleotide variants comprises at least 20 different polynucleotide variants.

13. The method of claim 1, wherein the plurality of polynucleotide variants comprises at least 200 different polynucleotide variants.

14. The method of claim 1, wherein the plurality of polynucleotide variants comprises at least 1000 different polynucleotide variants.

15. The method of claim 1, wherein the plurality of polynucleotide variants comprises at least 20 different polynucleotide variants each comprising a different defined nucleotide difference at one of 20 different selected positions.

16. The method of claim 15, wherein at least 75% of the synthesized plurality of polynucleotide variants comprise the correct sequence.

17. The method of claim 1, wherein the plurality of polynucleotide variants comprises at least 46 different polynucleotide variants each comprising one of 23 different codons at one of 2 different selected positions.

18. The method of claim 17, wherein at least 75% of the synthesized plurality of polynucleotide variants comprise the correct sequence.

19. The method of claim 1, wherein the plurality of polynucleotide variants comprises at least 460 different polynucleotide variants each comprising one of 23 different codons at one of 20 different selected positions.

20. The method of claim 19, wherein at least 75% of the synthesized plurality of polynucleotide variants comprise the correct sequence.

21. The method of claim 1, wherein at least one of the plurality of sets of amplicons comprises at least 5 different degenerate amplicons.

22. The method of claim 1, wherein the lengths of the forward and reverse primers are from about 20 to about 50 nucleotides.

23. The method of claim 1, wherein the length of the reference polynucleotide sequence is at least 1000 bp.

24. The method of claim 1, wherein sequences of the plurality of forward and reverse mutagenic primer sequences are generated by:
(i) identifying a first defined difference in the polynucleotide variant sequence as compared to the reference sequence, and determining the proximity of a nearest-neighbor defined difference in the polynucleotide sequence;
(ii) selecting a mutagenic forward primer having a sequence comprising the first defined nucleotide difference, and optionally including any nearest-neighbor defined difference in the same forward primer if proximate to the first defined nucleotide difference;
(iii) identifying a next defined difference in the polynucleotide variant sequence as compared to the reference sequence, and determining the proximity of a nearest-neighbor defined difference in the polynucleotide sequence, or identifying that the end of the polynucleotide variant has been reach;
(iv) selecting a reverse mutagenic primer having a sequence comprising the next defined nucleotide difference, and optionally including any nearest-neighbor defined difference in the same forward primer if proximate to the next defined nucleotide difference; and
(v) repeating steps (iii) to (iv) for each defined difference in the polynucleotide variant sequence such that all defined difference are present on primers.

25. The method of claim 24, wherein the method further comprises selecting non-mutagenic reverse and forward oligonucleotide primers for polynucleotide segments not defined by the forward and reverse mutagenic primers of (ii) and (iv).

* * * * *